(12) United States Patent
Clagett-Dame et al.

(10) Patent No.: US 8,404,667 B2
(45) Date of Patent: Mar. 26, 2013

(54) COMPOUNDS, COMPOSITIONS, KITS AND METHODS OF USE TO ORALLY AND TOPICALLY TREAT ACNE AND OTHER SKIN CONDITIONS BY 19-NOR VITAMIN D ANALOG

(75) Inventors: Margaret Clagett-Dame, Deerfield, WI (US); Hector F. DeLuca, Deerfield, WI (US); Nirca J. Nieves, Madison, WI (US); Lori A. Plum, Arena, WI (US); Mary E. Kaiser, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 225 days.

(21) Appl. No.: 11/966,504

(22) Filed: Dec. 28, 2007

(65) Prior Publication Data
US 2008/0261925 A1  Oct. 23, 2008

Related U.S. Application Data

(60) Provisional application No. 60/882,705, filed on Dec. 29, 2006, provisional application No. 61/017,217, filed on Dec. 28, 2007, provisional application No. 61/017,219, filed on Dec. 28, 2007.

(51) Int. Cl.
*A61K 31/59* (2006.01)
*A61P 35/00* (2006.01)
*A61P 17/06* (2006.01)
*A61P 17/00* (2006.01)

(52) U.S. Cl. ......................... 514/167; 552/653
(58) Field of Classification Search .................. 514/167; 552/552
See application file for complete search history.

(56) References Cited

U.S. PATENT DOCUMENTS
4,335,120 A  6/1982 Holick et al.
4,757,140 A  7/1988 DeLuca et al.
4,841,038 A  6/1989 DeLuca et al.

(Continued)

OTHER PUBLICATIONS

Dawson, M.I., et al., "Synthetic retinoids and their usefulness in biology and medicine," Vitamin A and retinoids: an update of biological aspects and clinical applications, M.A. Livrea (ed) 2000 Birkhauser Verlag Basel/Switzerland, pp. 161-196.

(Continued)

*Primary Examiner* — Sabiha N Qazi
(74) *Attorney, Agent, or Firm* — Quarles & Brady LLP

(57) ABSTRACT

Oral and topical pharmaceutical compositions, kits and methods of treatment thereof for treating various skin disorder including acne, psoriasis, ichthyosis, photoaging, photodamaged skin, and, skin cancer. Exemplary vitamin D analogs as active pharmaceutical ingredients include 2-methylene-19-nor-20(S)-1α-hydroxy-bishomopregnacalciferol, 19-nor-26,27-dimethylene-20(S)-2-methylene-1α,25-dihydroxyvitamin $D_3$, 2-methylene-1α,25-dihydroxy-(17E)-17(20)-dehydro-19-nor-vitamin $D_3$, 2-methylene-19-nor-(24R)-1α,25-dihydroxyvitamin $D_2$, 2-methylene-(20R,25S)-19,26-dinor-1α,25-dihydroxyvitamin $D_3$, 2-methylene-19-nor-1α-hydroxy-pregnacalciferol, 1α-hydroxy-2-methylene-19-nor-homopregnacalciferol, (20R)-1α-hydroxy-2-methylene-19-nor-bishomopregnacalciferol, 2-methylene-19-nor-(20S)-1α-hydroxy-trishomopregnacalciferol, 2-methylene-23,23-difluoro-1α-hydroxy-19-nor-bishomopregnacalciferol, 2-methylene-(20S)-23,23-difluoro-1α-hydroxy-19-nor-bishomopregnancalciferol, (2-(3'hydroxypropyl-1',2'-idene)-19,23,24-trinor-(20S)-1α-hydroxyvitamin $D_3$, 2-methylene-18,19-dinor-(20S)-1α,25-dihydroxyvitamin $D_3$, a stereoisomer thereof, a prodrug thereof in oral compositions, a salt thereof, and/or a solute thereof. Compounds that activate retinoic acid receptors, such as retinoyls and retinoyl esters, include 13-cis-retinoic acid, all-trans-retinoic acid, (2E,4E,6Z,8E)-3,7-dimethyl-9-(2,6,6-trimethyl-1-cyclohexeneyl)nona-2,4,6,8-tetraenoic acid, 9-(4-methoxy-2,3,6-trimethyl-phenyl)-3,7-dimethyl-nona-2,4,6,8-tetraenoic acid, 6-[3-(1-adamantyl)-4-methoxyphenyl]-2-napthoic acid, 4-[1-(3,5,5,8,8-pentamethyl-tetralin-2-yl)ethenyl]benzoic acid, retinobenzoic acid, ethyl 6-[2-(4,4-dimethylthiochroman-6-yl)ethynyl]pyridine-3-carboxylate, retinoyl t-butyrate, retinoyl pinacol, retinoyl cholesterol, an isomer thereof, a prodrug thereof for oral compositions, an ester thereof, a salt thereof, and/or, a solute thereof. Combinations of such active ingredients demonstrate synergistic efficacy.

23 Claims, 16 Drawing Sheets

U.S. PATENT DOCUMENTS

| | | | |
|---|---|---|---|
| 4,966,965 A | 10/1990 | DeLuca et al. | |
| 5,190,935 A | 3/1993 | Binderup et al. | |
| 5,362,719 A | 11/1994 | Godtfredsen | |
| 5,401,731 A | 3/1995 | Calverley et al. | |
| 5,545,633 A | 8/1996 | Bretting | |
| 5,710,142 A | 1/1998 | Calverley et al. | |
| 5,747,478 A | 5/1998 | Doran et al. | |
| 5,808,120 A | 9/1998 | DeLuca et al. | |
| 5,817,648 A | 10/1998 | Kutner et al. | |
| 5,880,292 A | 3/1999 | DeLuca et al. | |
| 5,998,394 A | 12/1999 | Voorhees et al. | |
| 6,080,878 A | 6/2000 | de los Angeles Rey et al. | |
| 6,207,656 B1 | 3/2001 | Carswell et al. | |
| 6,221,911 B1 | 4/2001 | Lavin et al. | |
| 6,242,435 B1 | 6/2001 | Achkar | |
| 6,329,538 B1 | 12/2001 | Batcho et al. | |
| 6,331,642 B1 | 12/2001 | Batcho et al. | |
| 6,440,953 B1 | 8/2002 | DeLuca et al. | |
| 6,452,028 B1 | 9/2002 | Batcho et al. | |
| 6,552,009 B2 | 4/2003 | Achkar | |
| 6,558,656 B2 | 5/2003 | Mann | |
| 6,566,352 B1 * | 5/2003 | DeLuca et al. | 514/167 |
| 6,573,255 B1 | 6/2003 | Bretting | |
| 6,627,622 B2 * | 9/2003 | DeLuca et al. | 514/167 |
| 6,696,431 B2 | 2/2004 | DeLuca et al. | |
| 6,753,013 B1 | 6/2004 | Didriksen et al. | |
| 6,774,251 B2 | 8/2004 | DeLuca et al. | |
| 6,787,529 B2 | 9/2004 | Hoy et al. | |
| 7,094,774 B2 * | 8/2006 | DeLuca et al. | 514/167 |
| 7,126,017 B2 | 10/2006 | DeLuca et al. | |
| 7,205,286 B2 * | 4/2007 | DeLuca et al. | 514/167 |
| 7,232,810 B2 | 6/2007 | DeLuca et al. | |
| 7,241,748 B2 * | 7/2007 | DeLuca et al. | 514/167 |
| 7,241,750 B2 * | 7/2007 | DeLuca et al. | 514/167 |
| 7,241,751 B2 | 7/2007 | DeLuca et al. | |
| 7,241,752 B2 | 7/2007 | DeLuca et al. | |
| 7,244,719 B2 * | 7/2007 | DeLuca et al. | 514/167 |
| 7,468,361 B2 * | 12/2008 | DeLuca et al. | 514/167 |
| 7,528,122 B2 * | 5/2009 | DeLuca et al. | 514/167 |
| 7,648,974 B1 * | 1/2010 | DeLuca et al. | 514/167 |
| 7,718,637 B2 * | 5/2010 | DeLuca et al. | 514/167 |
| 7,718,638 B2 * | 5/2010 | DeLuca et al. | 514/167 |
| 7,763,598 B2 * | 7/2010 | DeLuca et al. | 514/167 |
| 7,893,043 B2 * | 2/2011 | DeLuca et al. | 514/167 |
| 7,964,639 B2 * | 6/2011 | Deluca et al. | 514/529 |
| 8,093,232 B2 * | 1/2012 | Deluca et al. | 514/167 |
| 2001/0002396 A1 | 5/2001 | Achkar | |
| 2001/0056071 A1 | 12/2001 | Pelliccia et al. | |
| 2003/0158157 A1 | 8/2003 | DeLuca et al. | |
| 2004/0167215 A1 | 8/2004 | DeLuca et al. | |
| 2005/0070511 A1 | 3/2005 | DeLuca et al. | |
| 2005/0085539 A1 | 4/2005 | DeLuca et al. | |
| 2005/0119242 A1 | 6/2005 | DeLuca et al. | |
| 2005/0182144 A1 | 8/2005 | Biadatti et al. | |
| 2006/0135798 A1 | 6/2006 | DeLuca et al. | |
| 2006/0135799 A1 | 6/2006 | DeLuca et al. | |
| 2006/0189532 A1 | 8/2006 | DeLuca et al. | |
| 2007/0105774 A1 | 5/2007 | DeLuca et al. | |
| 2007/0244072 A1 | 10/2007 | Deluca et al. | |
| 2009/0258850 A1 | 10/2009 | Frincke et al. | |
| 2010/0120728 A1 | 5/2010 | Petkovich et al. | |
| 2010/0144684 A1 | 6/2010 | Bishop | |
| 2011/0039809 A1 | 2/2011 | Buck et al. | |
| 2012/0028934 A1 | 2/2012 | Cohen et al. | |

OTHER PUBLICATIONS

Plum, L.A., et al., "Biologically active noncalcemic analogs of 1alpha,25-dihydroxyvitamin D with an abbreviated side chain containing no hydroxyl," PNAS 18:6900-6904 (2004).
PCT International Search Report and Written Opinion, PCT/US2007/089193, May 11, 2009.
Intellectual Property Office of New Zealand, Examination Report, Patent Application No. 577962, Sep. 13, 2010.
Mexican Patent Office, Official Action, Patent Application No. MX/a/2009/007015, General Translation of the Requirements Stated by the Examiner, Sep. 28, 2010.
Akhavan, et al., 2003, Am. J. Clin. Dermatol. 4:473-492.
Akyol, et al., 2005, Am. J. Clin. Dermatol. 6(3):175-184.
Armstrong, et al., 1994, The Retinoids, pp. 545-572.
Blomhoff, et al., 1992, Annu. Rev. Nutr. 12:37-57.
Bouclier, et al., 1990, Pharmacological Reviews 42:127-154.
Chambon, 1996, FASEB J. 10:940-954.
Clagett-Dame, et al., 1997, Crit. Rev. Euk. Gene Exp. 7:299-342.
Clagett-Dame, et al., 2002, Annu. Rev. Nutr. 22:347-381.
DeLuca, 2004, Am. J. Clin. Nutr. 80(suppl):1689S-1696S.
DiGiovanna, 2001, J. Am. Acad. Dermatol. 45:S176-S182.
Fisher, et al., 1996, FASEB J. 10:1002-1013.
Fox, et al., 2006, Section XIII Dermatology, Chapter 62 Dermatological Pharmacology, pp. 1679-1706, Goodman & Gilman's: The Pharmacological Basis of Therapeutics, 11th Ed., McGraw-Hill Medical Publishing Division.
Holick, 1989, Arch. Dermatol. 125:1692-1697.
Mark, et al., 2006, Annu. Rev. Pharmacol. Toxicol. 46:451-480.
Mirshahpanah, et al., 2007, Cutaneous and Ocular Toxicology 26:195-202.
Moise, et al., 2007, Biochemistry 46:4449-4458.
Remington, The Science and Practice of Pharmacy, pp. 1131, 1288-1289, 1695-1696, Lippincott Williams & Wilkins, 21st Ed.
Repa, et al., 1993, Proc. Natl. Acad. Sci. USA 90:7293-7297.
Roberts, et al., 1967, Biochem. J. 102:600-605.
Shevde, et al., 2002, Proc. Natl. Acad. Sci. USA 99(21):13487-13491.
Sicinski, et al., 1998, J. Med. Chem. 41:4662-4674.
Smith, et al., 1988, J. Am. Acad. Dermatol. 19:516-528.
Lutzow-Holm, et al., 1,25-dihydroxyvitamin D3 and the Vitamin D Analogue KH1060 Induce Hyperproliferation in Normal Mouse Epidermis. A BrdUrd/DNA Flow Cytometric Study, Exp. Dermatol., 1993, 2:113-120.

* cited by examiner

COMPOUNDS, COMPOSITIONS, KITS AND METHODS OF USE TO ORALLY AND TOPICALLY TREAT ACNE AND OTHER SKIN CONDITIONS BY 19-NOR VITAMIN D ANALOG

CROSS REFERENCE TO RELATED APPLICATIONS

This application claims priority to and benefit of commonly-owned U.S. Provisional Application Ser. No. 60/882,705 filed on Dec. 29, 2006, which is also incorporated herein by reference.

This application also claims priority to and benefit of commonly-owned U.S. Provisional Application Ser. No. 61/017,217, filed on Dec. 28, 2007, entitled "(20S)-23,23-Difluoro-2-Methylene-19-Nor-Bishomopregnacalciferol-Vitamin D Analogs", which is also incorporated herein by reference.

This application also claims priority to and benefit of commonly-owned U.S. Provisional Application Ser. No. 61/017,219, filed on Dec. 28, 2007, entitled "(20R)-23,23-Difluoro-2-Methylene-19-Nor-Bishomopregnacalciferol-Vitamin D Analogs", which is also incorporated herein by reference.

This application is related to U.S. Application Publication No. US 2004/0167215, Ser. No. 10/758,767, filed Jan. 16, 2004.

This application is related to U.S. Pat. No. 7,126,017 issued on Oct. 24, 2006.

STATEMENT REGARDING GOVERNMENT INTEREST

Not applicable.

BACKGROUND OF THE INVENTION

Natural and synthetic retinoid compounds have been used to treat a variety of hyperproliferative skin disorders as well as other skin disorders including, for example, acne, psoriasis, wrinkling, sun-damaged skin, and age spots. (See Fox L P et al., Goodman & Gilman's: The Pharmacological Basis of Therapeutics, Section XIII-Dermatology, 11th Ed.) In many cases, retinoids have been applied topically. Retinoic acid has also been administered orally to treat severe cases of acne. For example, Accutane® contains 13-cis-retinoic acid, also referred to as isotretinoin, which is related to both retinoic acid and retinol, i.e., vitamin A. (See Remington, The Science and Practice of Pharmacy p. 1288-1289, $21^{st}$ Ed.). Accutane® has been approved for treating nodular acne by administering oral pharmacologic dosages of 0.5 to 2.0 mg/kg/day which inhibits sebaceous gland function and keratinization.

Retinoids are natural and synthetic compounds that are structurally related to vitamin A. All-trans retinol is the major circulating form of vitamin A. It is oxidized in the body: first to all-trans retinaldehyde, and then to all-trans retinoic acid (atRA). (Blomhoff et al., 1992, Annu. Rev. Nutr. 12:37-57; and, Moise et al., 2007, Biochemistry 46:4449-4458). atRA is the functional form of the vitamin that regulates growth, cellular differentiation, and embryonic development, whereas all-trans retinaldehyde functions in the visual cycle. (Clagett-Dame et al., 2002, Annu. Rev. Nutr. 22:347-381). Because atRA is such a potent regulatory molecule, it is formed in very small amounts, and it is rapidly metabolized such that its half-life is relatively short. (Roberts et al., 1967, Biochem. J. 102:600-605).

Systemic administration of retinoids has also been indicated for diseases such as pityriasis, rubra pilaris, condylomata accuminata, skin cancers, rosacea, hidradenitis, suppurativa, granuloma annular, lupus erythematosus and lichen planus. (Akyol M et al., 2006, Am. J. Clin. Derm. 6(3), 175-184).

Topical administration of retinoids has been limited largely due to side effects such as skin irritation (e.g., redness and burning), dryness and photosensitivity reactions. (Akhavan et al., 2003, Am. J. Clin. Dermatol. 4:473-492). Oral administration of retinoids has been even more limited due to more serious side effects such as teratogenicity (e.g., fetal malformation), elevation of triglyceride, cholesterol, and transaminase levels, bone demineralization, and other side effects associated with topical administration (e.g., drying of mucosal membranes and photosensitivity). (Armstrong et al., 1994, The Retinoids, pp. 545-572; and, DiGiovanna, 2001, J. Am. Acad. Dermatol. 45:S176-S182). Such numerous and varied sided effects have substantially limited the medical and pharmaceutical use of retinoids, particularly those related to skin therapies.

It is believed that retinoic acid and other synthetic retinoids bind to and regulate the transcriptional activity of a family of nuclear proteins known as the retinoic acid receptors ("RARs"). (Chambon, 1996, FASEB J. 10:940-954; Clagett-Dame et al., 1997, Crit. Rev. Euk. Gene Exp. 7:299-342; and, Mark et al., 2006, Annu. Rev. Pharmacol. Toxicol. 46:451-480). All-trans-retinoic acid is the endogenous ligand for the RAR family of receptors. The 13-cis retinoic acid isomer does not bind to the RARs. (Repa J J et al., 1993, Proc. Natl. Acad. Sci. USA 90:7293-7297). The 13-cis retinoic acid isomer must isomerize to all-trans-retinoic acid that is active in terms of receptor binding and activation.

It has been reported that the active hormonal form of vitamin D (i.e., calcitriol) and various synthetic analogs thereof demonstrate differentiative, antiproliferative and immunomodulatory activity. Such compounds have also demonstrated therapeutic efficacy in treating skin disease such as psoriasis. (See Smith E L et al, 1988, J. Am. Acad. Dermatol., 19, 516-528; and Holick, M F, 1989, Arch. Dermatol., 125, 1692-1697). It is also been reported that calcitriol and therapeutic analogs thereof are used to target the nuclear vitamin D receptor. (DeLuca H F, 2004, Am. J. Clin. Nutr. (Suppl) 1689S-1696S). It is believed that calcitriol and therapeutic analogs thereof may act directly within the epidermis on basal keratinocytes and Langerhans cells as well as on other cells within the immune system. The use of calcitriol and various synthetic analogs at therapeutic dosages is further limited by side effects such as hypercalcemia, hypercalcuria and calcification of soft tissues.

Recently, a new class of vitamin D analogs, referred to as 19-nor vitamin D compounds, has been discovered. 19-Nor vitamin D compounds are characterized by replacement of the A-ring exocyclic methylene group at the 19 carbon (in typical vitamin D molecules) with two hydrogens. Further substitution at the 2-position and/or modification of the side chain at 17 carbon of the five-membered ring has yielded pharmacologically active compounds that are much less calcemic at physiologically active concentrations as compared to the native hormone. (Plum, L. A. et al., Proc. Natl. Acad. Sci. USA, 101(18), 6900-9004 (2004)). Some 19-nor-containing vitamin D analogs have also exhibited enhanced potency and tissue selectivity activities suggesting that such analogs may have important therapeutic advantages over the native vitamin D hormone or other less-selective and/or non-selective analogs. (See Sicinski R R et al., 1998, J. Med. Chem., 41, 4662-4674; and, Shevde N K et al., 2002, Proc. Natl. Acad. Sci. USA, 99(21), 13487-13491).

Acne is a condition of the pilosebaceous unit. Acne involves a spectrum of effects including non-inflammatory comedones, inflammatory papules, pustules and cysts. When administered topically or systemically, retinoids cause epidermal hyperproliferation leading to comedolysis and improvement of the disease. (See Fisher G J et al., 1996, Molecular Mechanisms of Retinoid Actions in the Skin, *FASEB. J* 10:1002:21013). Although very effective, retinoid therapy is substantially limited by the number and extent of side effects, which are particularly limiting when retinoids are administered orally. (See Fox L P et al., 2006). Thus, there is an important and substantial need for retinoid-containing therapies having reduced side effects to treat various skin disorders such as acne.

SUMMARY OF THE INVENTION

One aspect of the invention is a topical dosage form composition comprising a therapeutically effective dose of an active pharmaceutical ingredient containing a 19-nor-containing vitamin D compound, a stereoisomer thereof, a salt thereof or a solute thereof, and, a pharmaceutically suitable topical carrier system.

In an exemplary embodiment of the topical dosage form composition, the 19-nor-containing vitamin D compound is one of the following compounds:

(2-methylene-19-nor-20(S)-1α-hydroxy-bishomopregnacalciferol that is also referred to herein as 2MBisP), (19-nor-26,27-dimethylene-20(S)-2-methylene-1α,25-dihydroxyvitamin $D_3$ that is also referred to herein as CAGE-3),

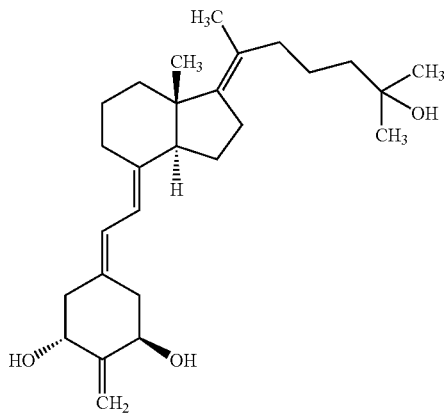 [SMILES: C=C1[C@H](O)CC(=C/C=C2\CCC[C@]3(C)/C(=C(\C)CCCC(C)(C)O)CC[C@@H]23)C[C@H]1O]

(2-methylene-1α,25-dihydroxy-(17E)-17(20)-dehydro-19-nor-vitamin $D_3$ that is also referred to herein as VitIII (17-20E)),

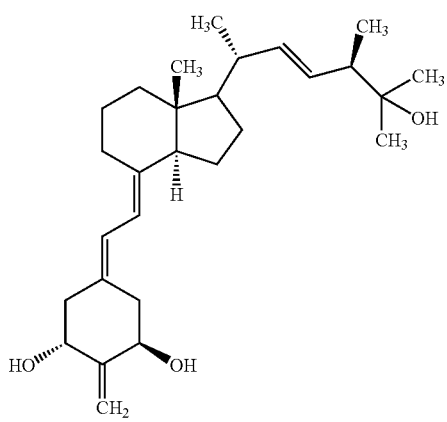 [SMILES: C=C1[C@H](O)CC(=C/C=C2\CCC[C@]3(C)C([C@H](C)/C=C/[C@@H](C)C(C)(C)O)CC[C@@H]23)C[C@H]1O]

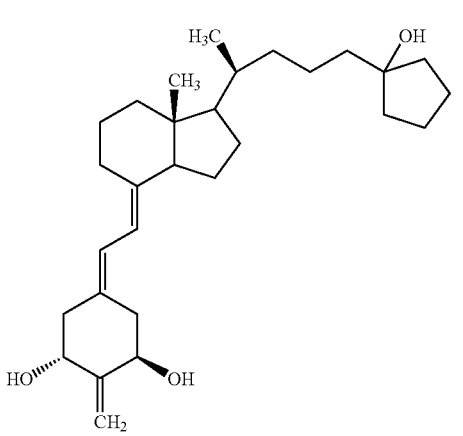

(2-methylene-19-nor-(24R)-1α,25-dihydroxyvitamin $D_2$ that is also referred to herein as 24R-2MD$_2$),

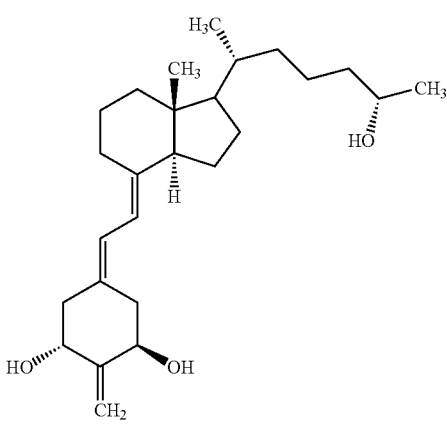 [SMILES: C=C1[C@H](O)CC(=C/C=C2\CCC[C@]3(C)C([C@H](C)CCC[C@H](C)O)CC[C@@H]23)C[C@H]1O]

(2-methylene-(20R,25S)-19,26-dinor-1α,25-dihydroxyvitamin $D_3$ that is also referred to herein as NEL),

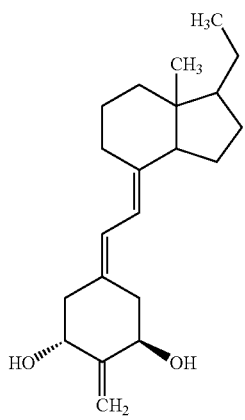 [SMILES: C=C1[C@H](O)CC(=C/C=C2\CCCC3(C)C(CC)CCC23)C[C@H]1O]

(2-methylene-19-nor-1α-hydroxy-pregnacalciferol that is referred to herein as 2MPregna),

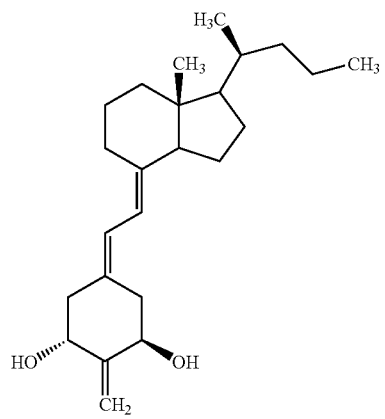

(2-methylene-(20S)-19-nor-1α-hydroxy-trishomopregna-calciferol that is referred to herein as 2MTrisP),

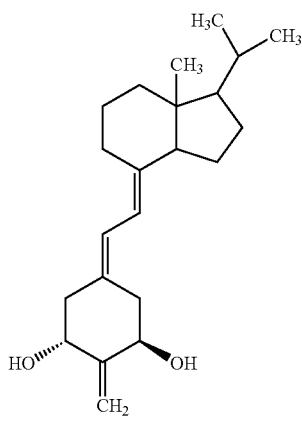 [SMILES: C=C1[C@H](O)CC(=C/C=C2\CCCC3(C)C2CCC3C(C)C)C[C@H]1O]

(1α-hydroxy-2-methylene-19-nor-homopregnacalciferol that is referred to herein as 2MP),

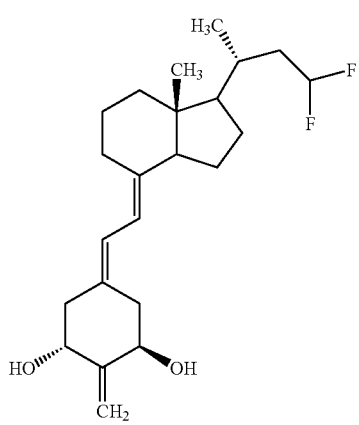

(2-methylene-(20R)-23,23-difluoro-1α-hydroxy-19-nor-bishomopregnacalciferol that is referred to herein as FF-44),

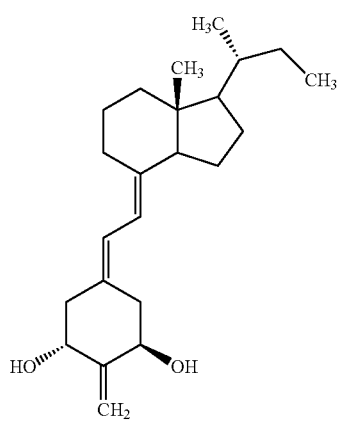 [SMILES: C=C1[C@H](O)CC(=C/C=C2\CCC[C@@]3(C)C2CCC3[C@H](C)CC)C[C@H]1O]

((20R)-1α-hydroxy-2-methylene-19-nor-bishomopregna-calciferol that is referred to herein as 20R-2MbisP),

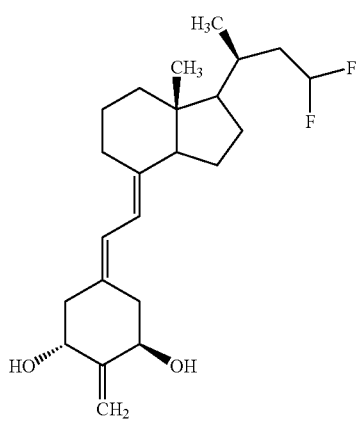 [SMILES: C=C1[C@H](O)CC(=C/C=C2\CCC[C@@]3(C)C2CCC3[C@@H](C)CC(F)F)C[C@H]1O]

(2-methylene-(20S)-23,23-difluoro-1α-hydroxy-19-nor-bishomopregnancalciferol that is referred to herein as FF-55),

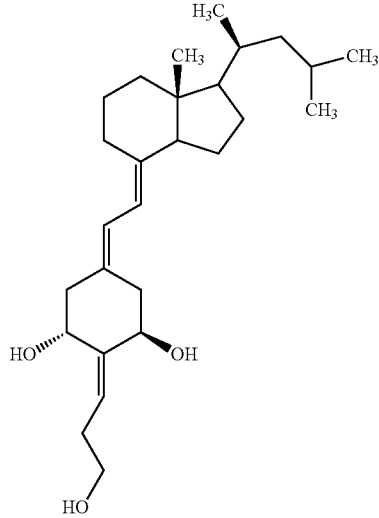 [SMILES: CC(C)C[C@H](C)C1CCC2/C(=C/C=C3C[C@@H](O)C(=CCCO)[C@H](O)C3)CCC[C@@]21C]

(2-(3'hydroxypropyl-1',2'-idene)-19,23,24-trinor-(20S)-1α-hydroxyvitamin $D_3$ that is referred to herein as HPBS),

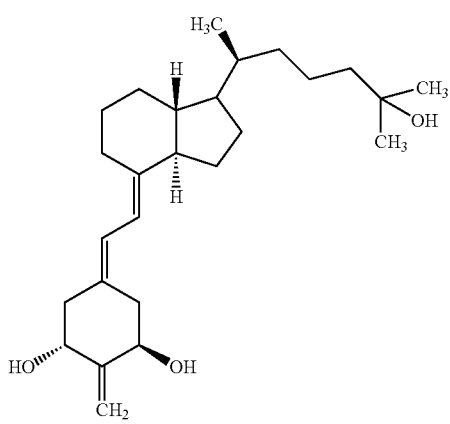 [SMILES: C=C1[C@H](O)CC(=C/C=C2\CCC[C@@H]3C([C@@H](C)CCCC(C)(C)O)CC[C@@H]23)C[C@H]1O]

(2-methylene-18,19-dinor-(20S)-1α,25-dihydroxyvitamin $D_3$ that is referred to herein as VD-03), a stereoisomer thereof, a salt thereof, and/or a solute thereof.

In another exemplary embodiment of the topical composition, the compound is

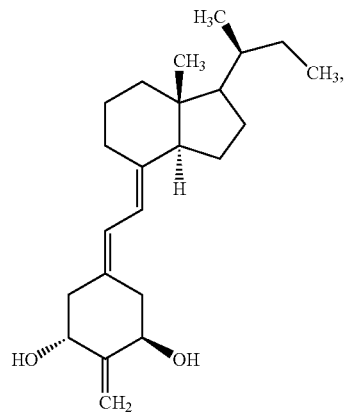

a stereoisomer thereof, a salt thereof or a solute thereof, and, the dose is in the range of 340 mg to 0.34 µg/kg$_{BW}$/day. In another exemplary embodiment of the topical composition, the carrier system comprises 30% to 70% ethanol and 70% to 30% propylene glycol. In another exemplary embodiment of the topical composition, the carrier system comprises 70% ethanol and 30% propylene glycol.

In another exemplary embodiment of the topical composition, the compound is

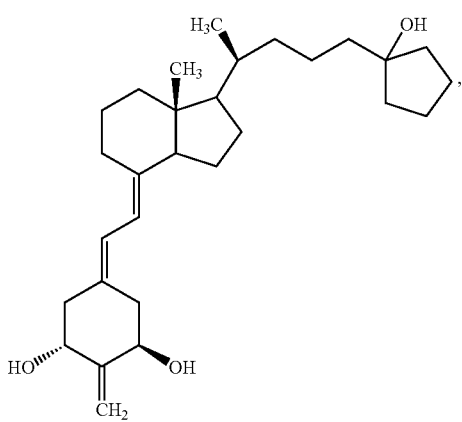 [SMILES: C=C1[C@H](O)CC(=C/C=C2\CCC[C@@]3(C)C2CCC3[C@@H](C)CCCC2(O)CCCC2)C[C@H]1O]

a stereoisomer thereof, a salt thereof, or a solute thereof, and, the dose is in the range of 14 µg to 14 pg/kg$_{BW}$/day. In another exemplary embodiment of the topical composition, the carrier system comprises 30% ethanol and 70% propylene glycol.

In another exemplary embodiment of the topical composition, the compound is

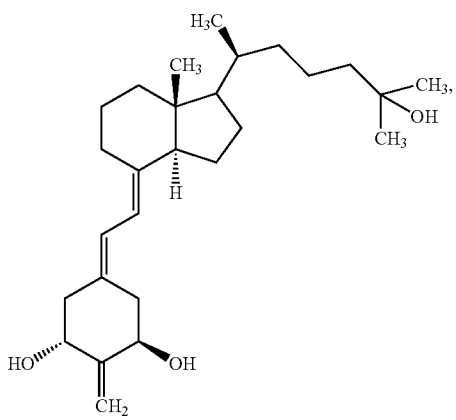

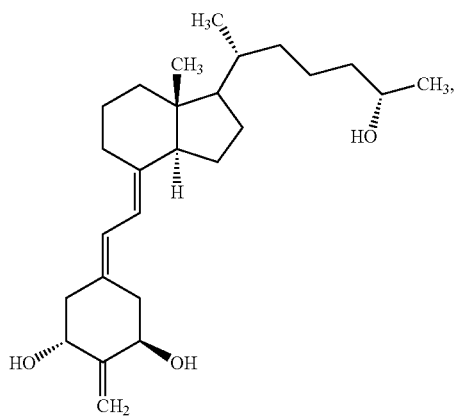

a stereoisomer thereof, a salt thereof or a solute thereof, and, the dose is in the range of 4.5 mg to 4.5 ng/kg$_{BW}$/day. In another exemplary embodiment of the topical composition, the carrier system comprises 70% ethanol and 30% propylene glycol.

In another exemplary embodiment of the topical composition, the compound is a stereoisomer thereof, a salt thereof, or a solute thereof, and, the dose is in the range of 4.5 mg to 4.5 ng/kg$_{BW}$/day. In another exemplary embodiment of the topical composition, the carrier system comprises 70% ethanol and 30% propylene glycol.

In another exemplary embodiment of the topical composition, the compound is

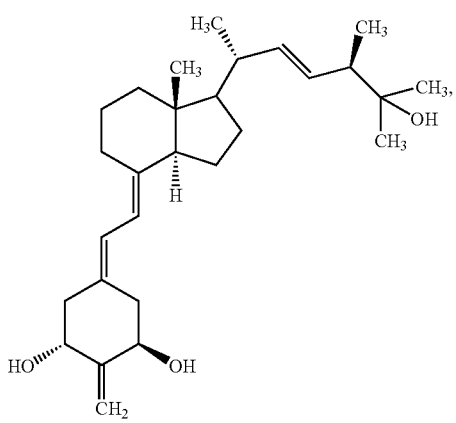

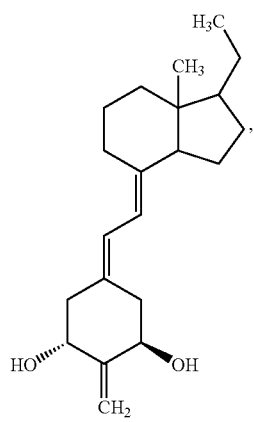 [SMILES: C=C1[C@H](O)CC(=C/C=C2\CCCC3(C)C(CC)CCC23)C[C@H]1O]

a stereoisomer thereof, a salt thereof, or a solute thereof, and, the dose is in the range of 450 μg to 0.45 ng/kg$_{BW}$/day. In another exemplary embodiment of the topical composition, the carrier system comprises 70% ethanol and 30% propylene glycol.

In another exemplary embodiment of the topical composition, the compound is a stereoisomer thereof, a salt thereof, or a solute thereof, and, the dose is in the range of 340 mg to 0.34 μg/kg$_{BW}$/day. In another exemplary embodiment of the topical composition, the carrier system comprises 70% ethanol and 30% propylene glycol.

In another exemplary embodiment of the topical composition, the compound is

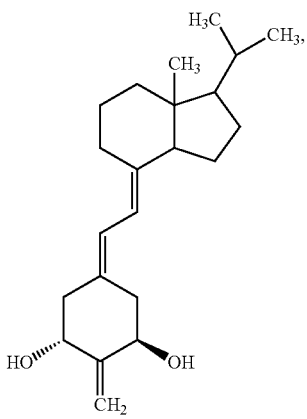

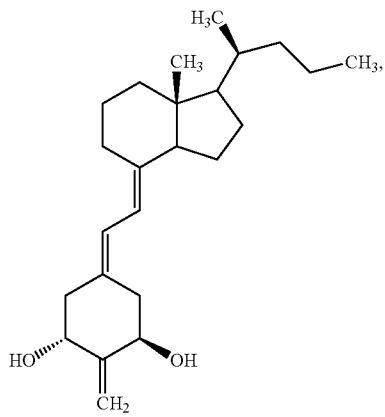

a stereoisomer thereof, a salt thereof, or a solute thereof, and, the dose is in the range of 340 mg to 0.34 μg/kg$_{BW}$/day. In another exemplary embodiment of the topical composition, the carrier system comprises 70% ethanol and 30% propylene glycol.

In another exemplary embodiment of the topical composition, the compound is a stereoisomer thereof, a salt thereof, or a solute thereof, and, the dose is in the range of 34 mg to 34 ng/kg$_{BW}$/day. In another exemplary embodiment of the topical composition, the carrier system comprises 70% ethanol and 30% propylene glycol.

In another exemplary embodiment of the topical composition, the compound is

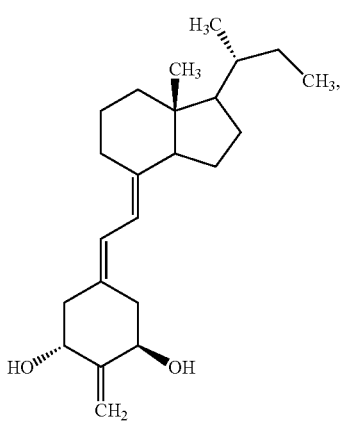

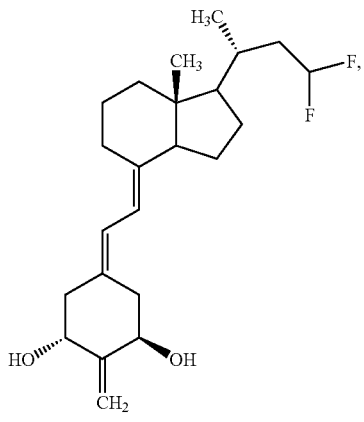

a stereoisomer thereof, a salt thereof, or a solute thereof, and wherein the dose is in the range of 340 mg to 0.34 pg/kg$_{BW}$/day. In another exemplary embodiment of the topical composition, the carrier system comprises 70% ethanol and 30% propylene glycol.

In another exemplary embodiment of the topical composition, the compound is a stereoisomer thereof, a salt thereof, or a solute thereof, and, the dose is in the range of 340 mg to 0.34 μg/kg$_{BW}$/day. In another exemplary embodiment of the topical composition, the carrier system comprises 70% ethanol and 30% propylene glycol.

In another exemplary embodiment of the topical composition, the compound is

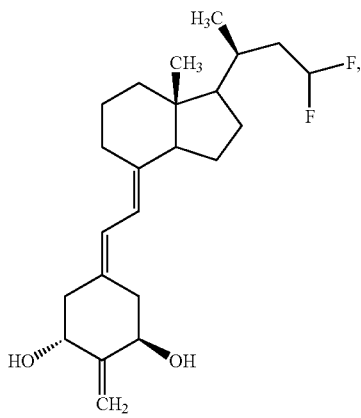

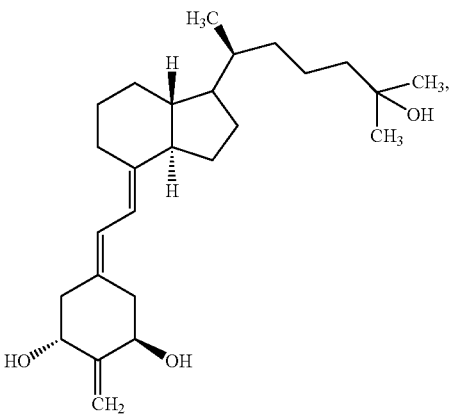

a stereoisomer thereof, a salt thereof, or a solute thereof, and, the dose is in the range of 340 mg to 0.34 μg/kg$_{BW}$/day. In another exemplary embodiment of the topical composition, the carrier system comprises 70% ethanol and 30% propylene glycol.

In another exemplary embodiment of the topical composition, the compound is

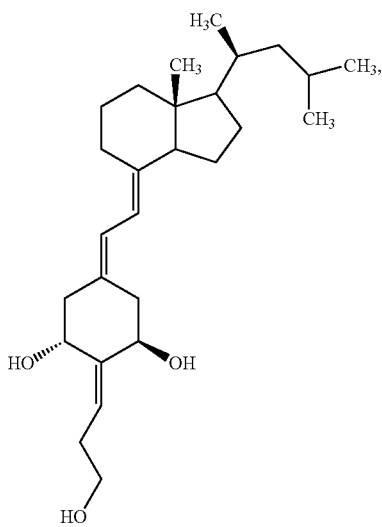

a stereoisomer thereof, a salt thereof, or a solute thereof, and, the dose is in the range of 41 mg to 41 ng/kg$_{BW}$/day. In another exemplary embodiment of the topical composition, the carrier system comprises 70% ethanol and 30% propylene glycol.

In another exemplary embodiment of the topical composition, the compound is a stereoisomer thereof, a salt thereof, or a solute thereof, and, the dose is in the range of 11 μg to 0.11 ng/kg$_{BW}$/day. In another exemplary embodiment of the topical composition, the carrier system comprises 70% ethanol and 30% propylene glycol.

Another aspect of the invention is a method of treating acne comprising the steps or acts of topically administering daily or intermittently any one of the topical compositions above to a human.

Another aspect of the invention is a method of reducing comedone area comprising the steps or acts of topically administering daily or intermittently any one of the topical compositions above to a human.

Another aspect of the invention is a method of treating psoriasis comprising the steps or acts of topically administering daily or intermittently any one of the topical compositions above to a human.

Another aspect of the invention is a method of treating ichthyosis comprising the steps or acts of topically administering daily or intermittently any one of the topical compositions above to a human.

Another aspect of the invention is a method of treating photoaging or photodamaged skin comprising the steps or acts of topically administering daily or intermittently any one of the topical compositions above to a human.

Another aspect of the invention is a method of treating skin cancer comprising the steps or acts of topically administering daily or intermittently any one of the topical compositions above to a human.

Another aspect of the invention is an oral dosage form composition comprising a therapeutically effective dose of an active pharmaceutical ingredient comprising a 19-nor-containing vitamin D compound, a stereoisomer thereof, a prodrug thereof, a salt thereof or a solute thereof, and, a pharmaceutically suitable oral carrier system.

In an exemplary embodiment of the oral composition, the 19-nor-containing vitamin D compound is one of the following compounds:

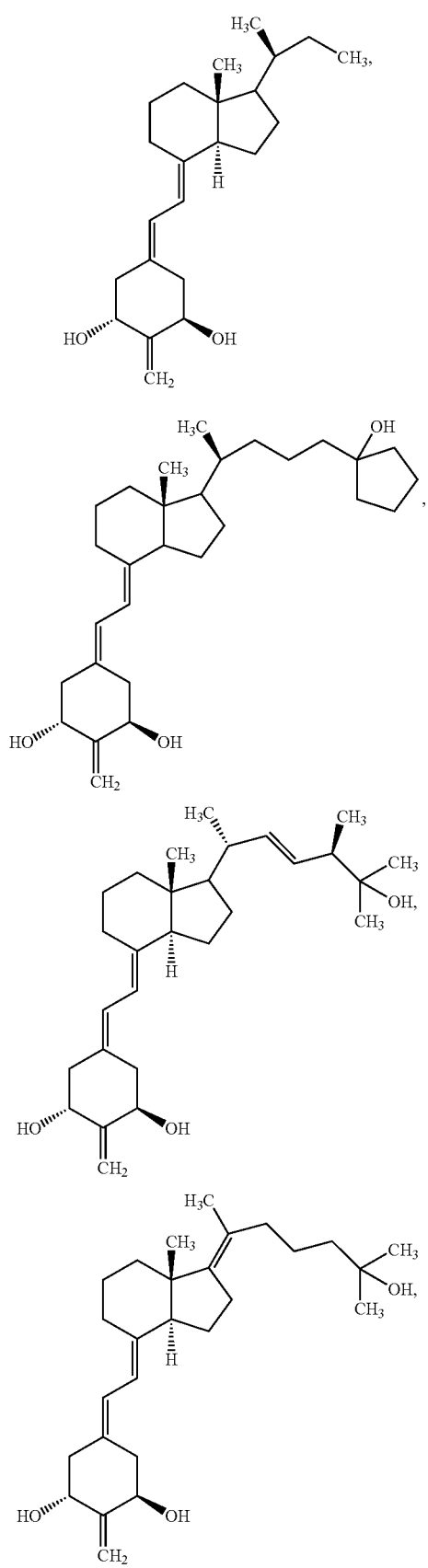

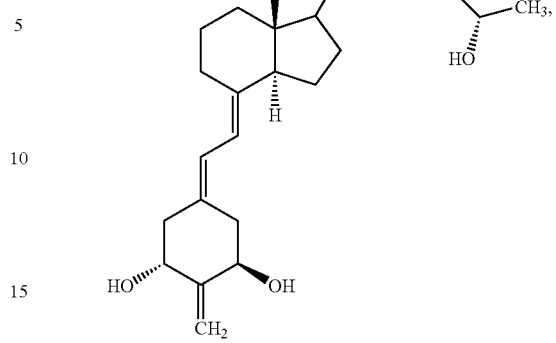

a stereoisomer thereof, a prodrug thereof, a salt thereof, and/or a solute thereof.

In another exemplary embodiment of the oral composition, the compound is

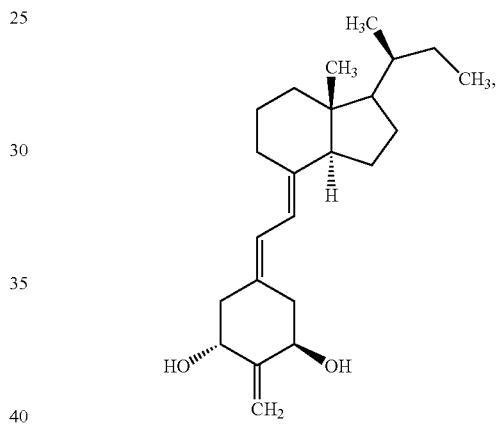

a stereoisomer thereof, a prodrug thereof, a salt thereof, or a solute thereof, and, the dose is in the range of 7.0 mg to 7.0 ng/kg$_{BW}$/day. In another exemplary embodiment of the oral composition, the carrier system comprises an oil.

In another exemplary embodiment of the oral composition, the compound is

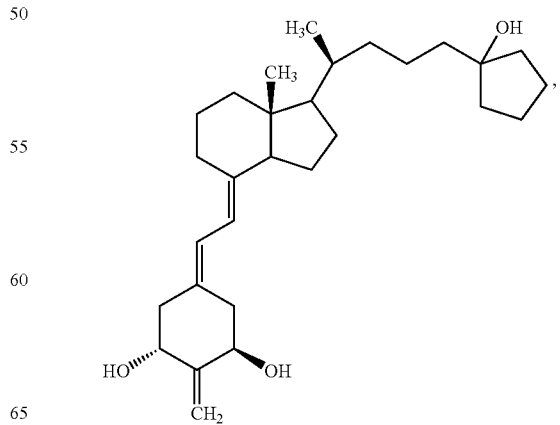

a stereoisomer thereof, a prodrug thereof, a salt thereof, or a solute thereof, and, the dose is 700 ng to 0.7 pg/kg$_{BW}$/day.

In another exemplary embodiment of the oral composition, the compound is

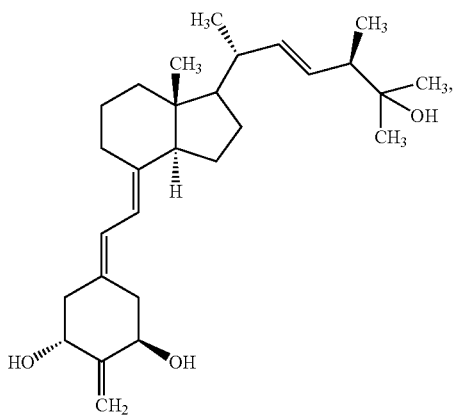

a stereoisomer thereof, a prodrug thereof, a salt thereof or a solute thereof, and, the dose is in the range of 23 μg to 23 pg/kg$_{BW}$/day.

In another exemplary embodiment of the oral composition, the compound is

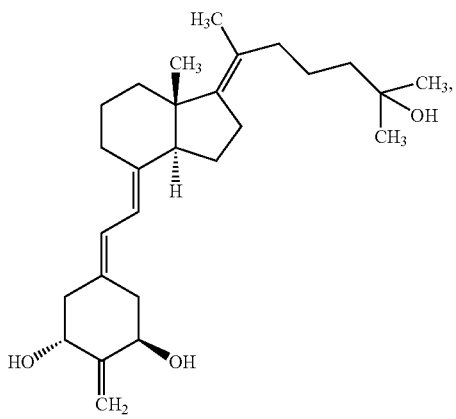

a stereoisomer thereof, a prodrug thereof, a salt thereof, or a solute thereof, and, the dose is in the range of 230 μg to 230 pg/kg$_{BW}$/day.

In another exemplary embodiment of the oral composition, the compound is

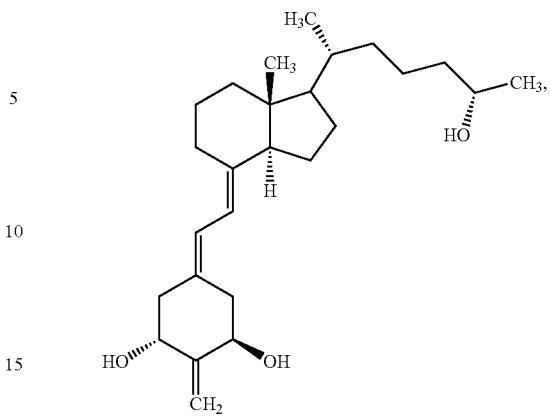

a stereoisomer thereof, a prodrug thereof, a salt thereof, or a solute thereof, and wherein the dose is in the range of 230 μg to 230 pg/kg$_{BW}$/day.

Another aspect of the invention is a method of treating acne comprising the steps or acts of orally administering daily or intermittently any one of the oral compositions above to a human.

Another aspect of the invention is a method of reducing comedone area comprising the steps or acts of orally administering daily or intermittently any one of the oral compositions above to a human.

Another aspect of the invention is a method of treating psoriasis comprising the steps or acts of orally administering daily or intermittently any one of the oral compositions above to a human.

Another aspect of the invention is a method of treating ichthyosis comprising the steps or acts of orally administering daily or intermittently any one of the oral compositions above to a human.

Another aspect of the invention is a method of treating photoaging or photodamaged skin comprising the steps or acts of orally administering daily or intermittently any one of the oral compositions above to a human.

Another aspect of the invention is a method of treating skin cancer comprising the steps or acts of orally administering daily or intermittently any one of the oral compositions above to a human.

Another aspect of the invention is a pharmaceutical kit comprising an oral dosage form composition comprising a first therapeutically effective dose of a first pharmaceutical active ingredient comprising a compound or prodrug thereof that activates the retinoic acid receptor including, for example, a retinoic acid compound, an isomer thereof, an ester thereof, a salt thereof, or a solute thereof, and, a pharmaceutically suitable oral carrier system, and, a topical dosage form composition comprising a second therapeutically effective amount of a second active pharmaceutical ingredient comprising a 19-nor-containing vitamin D compound, a stereoisomer thereof, a prodrug thereof, a salt thereof or a solute thereof, and, a pharmaceutically suitable topical carrier system.

In an exemplary embodiment of the pharmaceutical kit, the 19-nor-containing vitamin D compound is one of the following compounds:

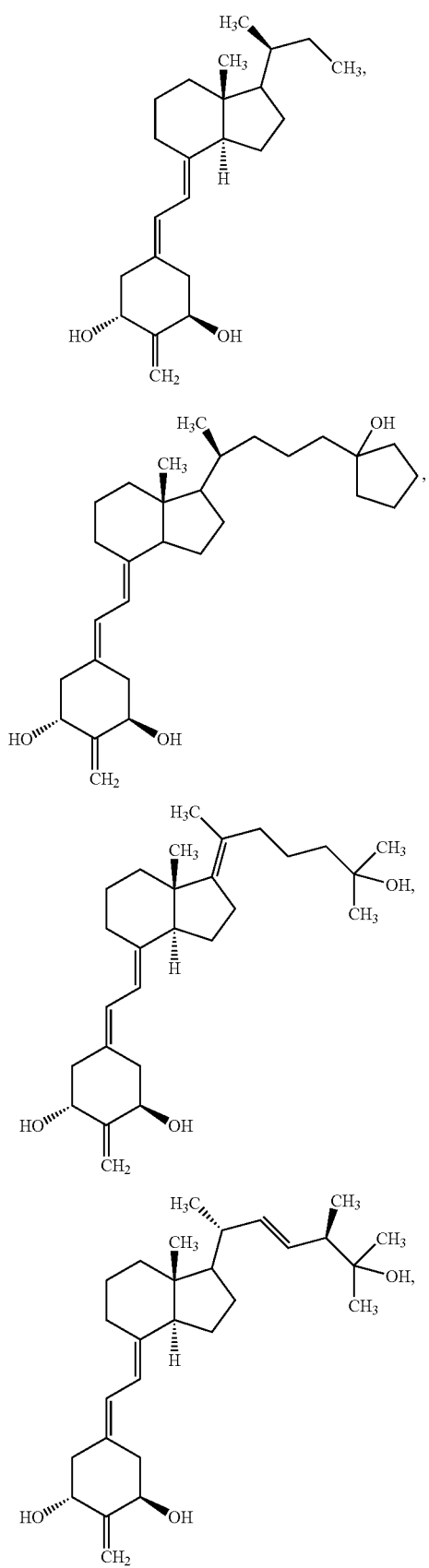
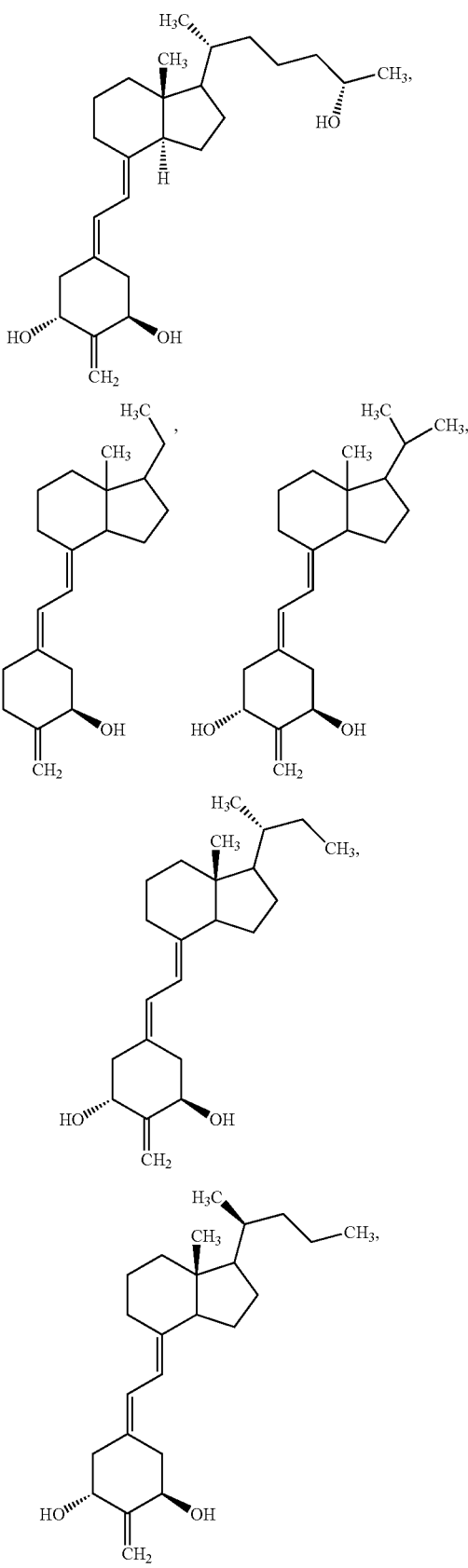

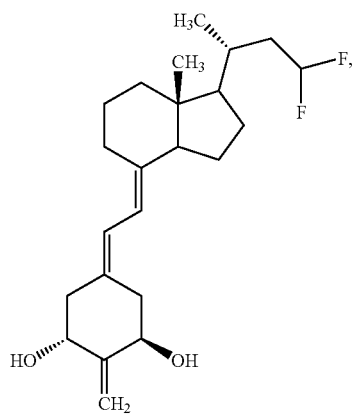

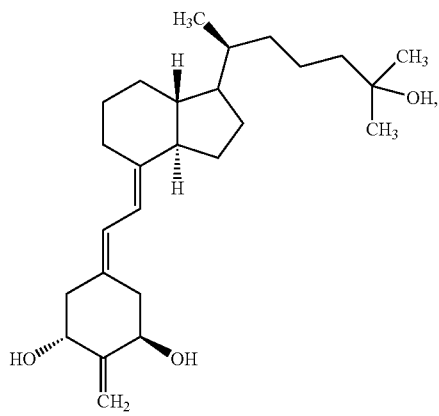

a stereoisomer thereof, a salt thereof, and/or a solute thereof.

In another exemplary embodiment of the pharmaceutical kit, the compound or prodrug thereof that activates the retinoic acid receptor is one of the following compounds:

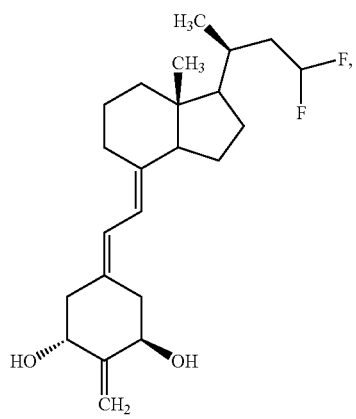

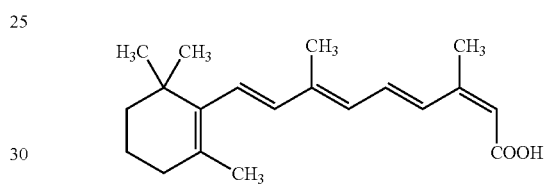

(13-cis-retinoic acid that is also referred to as isotretinoin and that is the active ingredient in Roaccutane®, Annesteem®, Claravis®, Sortret® and Accutane®),

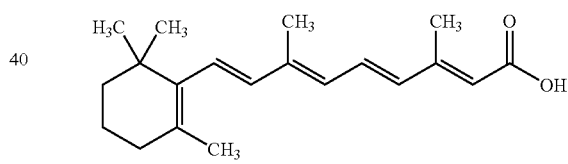

(all-trans-retinoic acid that is also referred to as tretinoin) (all-trans RA was used in the experiments because it is the active form derived from the prodrug, 13-cis RA that is approved for oral use),

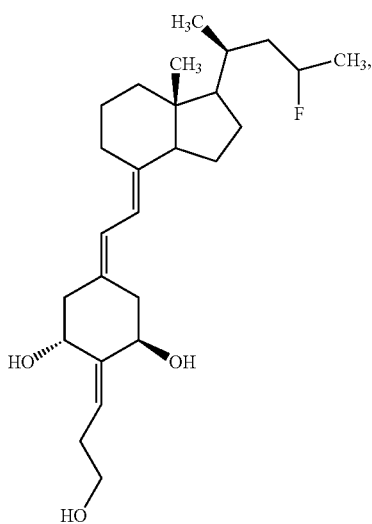

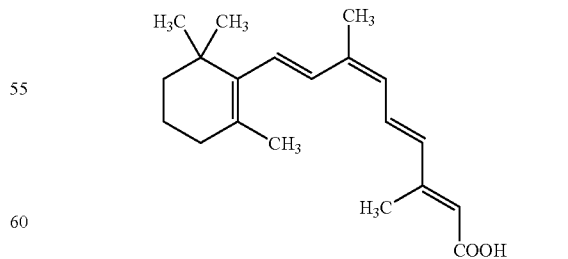

((2E,4E,6Z,8E)-3,7-dimethyl-9-(2,6,6-trimethyl-1-cyclohexenyl)nona-2,4,6,8-tetraenoic acid that is also referred to as 9-cis-retinoic acid and alitretinoin and that is the active ingredient in Panretin®),

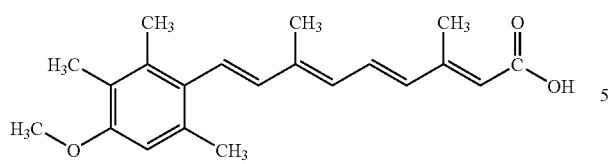

(9-(4-methoxy-2,3,6-trimethyl-phenyl)-3,7-dimethyl-nona-2,4,6,8-tetraenoic acid and that is also referred to as acitretin and that is the active ingredient in Soriatane®),

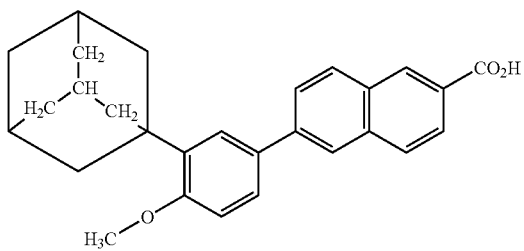 [SMILES: COc1ccc(-c2ccc3cc(C(=O)O)ccc3c2)cc1C12CC3CC(CC(C3)C1)C2]

(6-[3-(1-adamantyl)-4-methoxyphenyl]-2-napthoic acid that is also referred to as adapalene and CD417 and that is the active ingredient in Differin®),

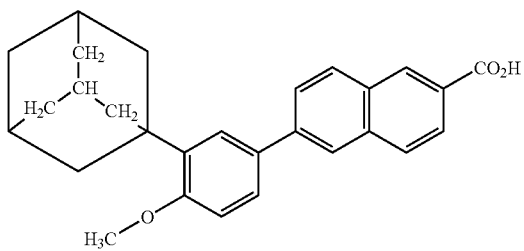 [SMILES: COc1ccc(-c2ccc3cc(C(=O)O)ccc3c2)cc1C12CC3CC(CC(C3)C1)C2]

(4-[1-(3,5,5,8,8-pentamethyl-tetralin-2-yl)ethenyl]benzoic acid that is also referred to as bexarotene and LGD1069 and that is the active ingredient in Targretin®),

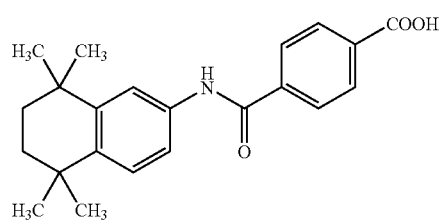 [SMILES: CC1(C)CCC(C)(C)c2cc(NC(=O)c3ccc(C(=O)O)cc3)ccc21]

(retinobenzoic acid that is also referred to as tamibarotene and that is the active ingredient in Amnoid®),

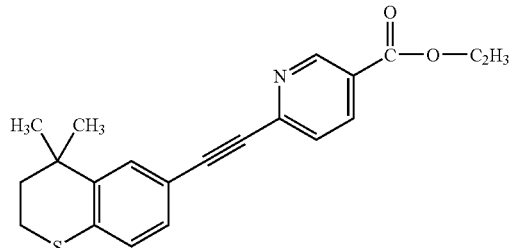

(ethyl 6-[2-(4,4-dimethylthiochroman-6-yl)ethynyl]pyridine-3-carboxylate that is also referred to as tazarotene and that is the active ingredient in Tazorac®, Avage®, and Zorac®).

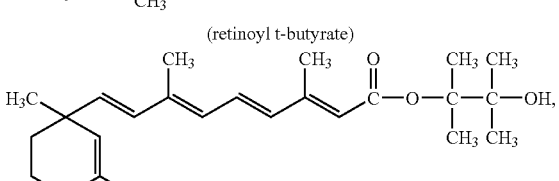

(retinoyl t-butyrate)

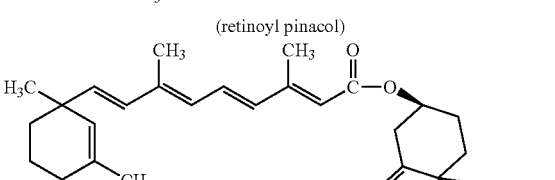

(retinoyl pinacol)

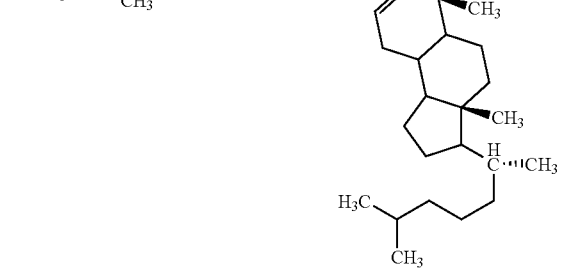

(retinoyl cholesterol), an isomer thereof, an ester thereof, a salt thereof, and/or, a solute thereof.

Another aspect of the invention is a pharmaceutical kit comprising an oral dosage form composition comprising a first therapeutically effective dose of a first active pharmaceutical ingredient comprising a compound according to the formula

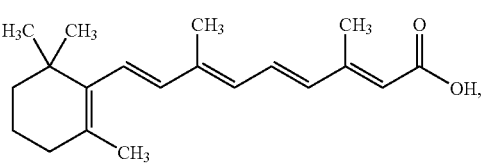

a prodrug thereof, an isomer thereof, an ester thereof, a salt thereof, or a solute thereof, and, a pharmaceutically suitable oral carrier system, and, a topical dosage form composition comprising a second therapeutically effective dose of a second active pharmaceutical ingredient comprising a compound according to the formula

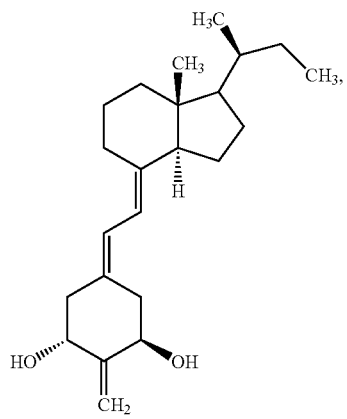

a stereoisomer thereof, a salt thereof, or a solute thereof, and, a pharmaceutically suitable topical carrier system.

In an exemplary embodiment of the kit, the first therapeutically effective dose is in the range of 5 ng/kg$_{BW}$/day to 1 mg/kg$_{BW}$/day, and the second therapeutically effective dose is in the range of 340 mg to 0.34 µg/kg$_{BW}$/day.

In another exemplary embodiment of the kit, the topical carrier system comprises 30% to 70% ethanol and 70% to 30% propylene glycol.

In another exemplary embodiment of the kit, the topical carrier system comprises 70% ethanol and 30% propylene glycol.

Another aspect of the invention is a pharmaceutical kit comprising an oral dosage form composition comprising a first therapeutically effective dose of a first active pharmaceutical ingredient comprising a compound according to the formula

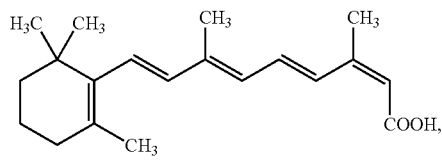

a prodrug thereof, an isomer thereof, an ester thereof, a salt thereof, or a solute thereof, and, a pharmaceutically suitable oral carrier system, and, a topical dosage form composition comprising a second therapeutically effective dose of a second active pharmaceutical ingredient comprising a compound according to the formula

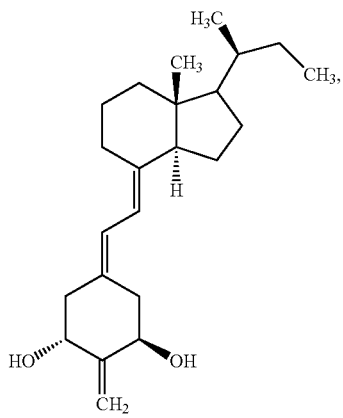

a stereoisomer thereof, a salt thereof, or a solute thereof, and, a pharmaceutically suitable topical carrier system. In an exemplary embodiment of the pharmaceutical kit, the first therapeutically effective dose is in the range of 50 ng/kg$_{BW}$/day to 10 mg/kg$_{BW}$/day, and the second therapeutically effective dose is in the range of 340 mg to 0.34 µg/kg$_{BW}$/day. In another exemplary embodiment of the pharmaceutical kit, the topical carrier system comprises 30% to 70% ethanol and 70% to 30% propylene glycol. In another exemplary embodiment of the pharmaceutical kit, the topical carrier system comprises 70% ethanol and 30% propylene glycol.

Another aspect of the invention is a method of treating acne comprising the steps or acts of administering daily or intermittently any one of the kits above to a human.

Another aspect of the invention is a method of reducing comedone area comprising the steps or acts of administering daily or intermittently any one of the kits above to a human.

Another aspect of the invention is a method of treating psoriasis comprising the steps or acts of administering daily or intermittently any one of the kits above to a human.

Another aspect of the invention is a method of treating ichthyosis comprising the steps or acts of administering daily or intermittently any one of the kits above to a human.

Another aspect of the invention is a method of treating photoaging or photodamaged skin comprising the steps or acts of administering daily or intermittently any one of the kits above a human.

Another aspect of the invention is a method of treating skin cancer comprising the steps or acts of administering daily or intermittently any one of the kits above to a human.

DETAILED DESCRIPTION OF THE EXEMPLARY EMBODIMENTS

Figure 1:
FIG. 1 illustrates the comedone area determination, whereby the area of each comedone is determined using a MetaMorph® Imaging System, whereby the system provides the area values for each individual comedone in pixels (see delineated inset area), and whereby the system is more accurate than prior comedone profiling techniques.
Figure 1:

There exists a need for improved therapeutic agents, either oral or topical, that maintain efficacy of existing therapies while also having an improved toxicity profile.

The invention is generally directed at oral and topical pharmaceutical compositions, kits and methods of treatment thereof for treating various skin disorder including acne, psoriasis, ichthyosis, photoaging, photodamaged skin, and, skin cancer. Exemplary vitamin D analogs as active pharmaceutical ingredients include 2-methylene-19-nor-20(S)-1α-hydroxy-bishomopregnacalciferol, 19-nor-26,27-dimethylene-20(S)-2-methylene-1α,25-dihydroxyvitamin $D_3$, 2-methylene-1α,25-dihydroxy-(17E)-17(20)-dehydro-19-nor-vitamin $D_3$, 2-methylene-19-nor-(24R)-1α,25-dihydroxyvitamin $D_2$, 2-methylene-(20R,25S)-19,26-dinor-1α,25-dihydroxyvitamin $D_3$, 2-methylene-19-nor-1α-hydroxypregnacalciferol, 1α-hydroxy-2-methylene-19-nor-homopregnacalciferol, (20R)-1α-hydroxy-2-methylene-19-nor-bishomopregnacalciferol, 2-methylene-19-nor-(20S)-1α-hydroxy-trishomopregnacalciferol, 2-methylene-23,23-difluoro-1α-hydroxy-19-nor-bishomopregnacalciferol, 2-methylene-(20S)-23,23-difluoro-1α-hydroxy-19-nor-bishomopregnancalciferol, (2-(3'hydroxypropyl-1',2'-idene)-19,23,24-trinor-(20S)-1α-hydroxyvitamin $D_3$, 2-methylene-18,19-dinor-(20S)-1α,25-dihydroxyvitamin $D_3$, a stereoisomer thereof, a prodrug thereof in oral compositions, a salt thereof, and/or a solute thereof. Compounds that activate retinoic acid receptors, such as retinoyls and retinoyl esters, include 13-cis-retinoic acid, all-trans-retinoic acid, (2E,4E,6Z,8E)-3,7-dimethyl-9-(2,6,6-trimethyl-1-cyclohexeneyl)nona-2,4,6,8-tetraenoic acid, 9-(4-methoxy-2,3,6-trimethyl-phenyl)-3,7-dimethyl-nona-2,4,6,8-tetraenoic acid, 6-[3-(1-adamantyl)-4-methoxyphenyl]-2-napthoic acid, 4-[1-(3,5,5,8,8-pentamethyl-tetralin-2-yl)ethenyl]benzoic acid, retinobenzoic acid, ethyl 6-[2-(4,4-dimethylthiochroman-6-yl)ethynyl]pyridine-3-carboxylate, retinoyl t-butyrate, retinoyl pinacol, retinoyl cholesterol, an isomer thereof, a prodrug thereof for oral compositions, an ester thereof, a salt thereof, and/or, a solute thereof. Combinations of such active ingredients demonstrate synergistic efficacy.

2-Methylene-19-nor-20(S)-1α-hydroxy-bishomopregnacalciferol (2MBisP) and methods of making the compound are disclosed in U.S. patent application Ser. No. 11/283,163 filed on Nov. 22, 2005, which is incorporated herein by reference. Salts and solutes of 2-methylene-19-nor-20(S)-1α-hydroxy-bishomopregnacalciferol (and other vitamin D analogs herein) can be made using conventional synthetic methods well known in the art. 2-Methylene-19-nor-20(S)-1α-hydroxy-bishomopregnacalciferol is also discussed in Plum, L. A. et al., Biologically active noncalcemic analogs of 1α,25-dihydroxyvitamin D with an abbreviated side chain containing no hydroxyl, PNAS vol. 101, no. 18, 6900-6904 (May 4, 2004).

19-Nor-26,27-dimethylene-20(S)-2-methylene-1α,25-dihydroxyvitamin $D_3$ (CAGE-3) and methods of making the compound are disclosed in U.S. Pat. No. 6,696,431, which is incorporated herein by reference. Salts and solutes of 19-nor-26,27-dimethylene-20(S)-2-methylene-1α,25-dihydroxyvitamin $D_3$ may also be made using conventional synthetic methods well known in the art.

2-methylene-1α,25-dihydroxy-(17E)-17(20)-dehydro-19-nor-vitamin $D_3$ (VitIII (17-20E)) and methods of making the compound are disclosed in U.S. Patent Application Publication Nos. 2006/0111330 and 2006/0116351, which are incorporated herein by reference. Salts and solutes of VitIII (17-20E) may also be made using conventional synthetic methods well known in the art.

2-methylene-19-nor-(24R)-1α,25-dihydroxyvitamin $D_2$ (24R-2MD$_2$) and methods of making the compound are disclosed in U.S. Pat. No. 7,232,810, which is incorporated herein by reference. Salts, stereoisomers, prodrugs and solutes of 24R-2MD$_2$ and the other 19-nor containing vitamin D compounds herein may also be made using conventional synthetic methods well known in the art.

2-methylene-(20R,25S)-19,26-dinor-1α,25-dihydroxyvitamin $D_3$ (NEL) and methods of making the compound are disclosed in commonly-owned U.S. patent application Ser. No. 11/669,029, filed Jan. 30, 2007 (US 2007/0191316), which is incorporated herein by reference. Salts and solutes of NEL may also be made using conventional synthetic method well known in the art.

2MPregna and methods of making the compound are disclosed in commonly-owned U.S. Pat. No. 6,566,352, which is incorporated herein by reference.

2MP and methods of making the compound are disclosed in commonly-owned U.S. Pat. No. 6,774,251, which is incorporated herein by reference.

20R-2MbisP and methods of making the compound are disclosed in commonly-owned U.S. patent application Ser. No. 11/282,972, which is incorporated herein by reference.

2MTrisP and methods of making the compound are disclosed in commonly-owned U.S. patent application Ser. No. 11/282,304, filed on Nov. 18, 2005, which is incorporated herein by reference.

FF-44 and methods of making the compound are disclosed commonly-owned in U.S. Provisional Patent Application No. 61/017,219, filed on Dec. 28, 2007, which is incorporated herein by reference.

FF-55 and methods of making the compound are disclosed in commonly-owned U.S. Provisional Patent Application No. 61/017,217, filed on Dec. 28, 2007, which is incorporated herein by reference.

HPBS and methods of making the compound are disclosed in commonly-owned U.S. patent application Ser. No. 11/732,924, filed on Apr. 5, 2007, which is incorporated herein by reference.

VD-03 and methods of making the compound are disclosed in commonly-owned U.S. Patent Application Publication Nos. 2006/0189532 and 2007/0105774, which are both incorporated herein by reference.

U.S. Patent Application Publication No. 2005/0119242 also discloses methods of making and using several of the 19-nor-containing compounds used herein, which is also incorporated herein.

All-trans-retinoic acid (atRA) is a commercially available API in products such as Vesanoid®. Methods of making synthetic atRA and salts, esters and solutes thereof are well known in the art. Salts, esters, isomers, prodrugs and solutes of atRA and the other retinoids herein may also be made using conventional synthetic methods well known in the art.

Retinoid compounds, analogs and derivatives thereof, as used herein, refer to vitamin A and its analogs, whereby the retinoid compounds, analogs and derivatives thereof function by binding to and regulating transcriptional activity of RAR. (See also *Remingtons* p. 1695-1696). Various retinoid compounds and methods thereof useful in the invention are disclosed in U.S. Pat. Nos. 4,841,038; 5,880,292; 4,757,140; 5,808,120; and, 4,966,965, and U.S. Patent Application Publication No. US2005/0085539, which are all incorporated herein by reference. Other retinoid/retinoyl, modified retinoid/retinoyl and retinoid/retinoyl ester compounds useful in the invention are disclosed in U.S. Pat. No. 7,126,017 and U.S. Patent Application Publication 2004/0167215, which are hereby incorporated herein by reference.

As used herein, "therapeutically effective dose" and "administering to a human a therapeutically effective dose" refers to an amount of one or more APIs sufficient to treat (e.g., prophylactic, treating the active condition or curing) one or more of acne vulgaris, psoriasis, ichthyosis, photoaging, photodamaged skin, and skin cancer.

As used herein, the phrase "compounds and prodrugs thereof that activate the retinoic acid receptor including, for example, a retinoic acid" and the like means compounds that bind to and regulate the transcriptional activity of a family of nuclear proteins known as the retinoic acid receptors ("RARs"). (Chambon, 1996, *FASEB J.* 10:940-954; Clagett-Dame et al., 1997, *Crit. Rev. Euk. Gene Exp.* 7:299-342; and, Mark et al., 2006, *Annu. Rev. Pharmacol. Toxicol.* 46:451-480).

The pharmaceutically suitable topical and oral carrier systems (also referred to as drug delivery systems, which are modern technology, distributed with or as a part of a drug product that allows for the uniform release or targeting of drugs to the body) preferably include FDA-approved and/or USP-approved inactive ingredients. Under 21 CFR 210.3(b)(8), an inactive ingredient is any component of a drug product other than the active ingredient. According to 21 CFR 210.3(b)(7), an active ingredient is any component of a drug product intended to furnish pharmacological activity or other direct effect in the diagnosis, cure, mitigation, treatment, or prevention of disease, or to affect the structure or any function of the body of humans or other animals. Active ingredients include those components of the product that may undergo chemical change during the manufacture of the drug product and be present in the drug product in a modified form intended to furnish the specified activity or effect. As used herein, a kit (also referred to as a dosage form) is a packaged collection of related material.

As used herein, the topical dosage form includes various dosage forms known in the art such as lotions (an emulsion, liquid dosage form, whereby this dosage form is generally for external application to the skin), lotion augmented (a lotion dosage form that enhances drug delivery, whereby augmentation does not refer to the strength of the drug in the dosage form), gels (a semisolid dosage form that contains a gelling agent to provide stiffness to a solution or a colloidal dispersion, whereby the gel may contain suspended particles), ointments (a semisolid dosage form, usually containing <20% water and volatiles5 and >50% hydrocarbons, waxes, or polyols as the vehicle, whereby this dosage form is generally for external application to the skin or mucous membranes), ointment augmented (an ointment dosage form that enhances drug delivery, whereby augmentation does not refer to the strength of the drug in the dosage form), creams (an emulsion, semisolid dosage form, usually containing >20% water and volatiles5 and/or <50% hydrocarbons, waxes, or polyols as the vehicle, whereby this dosage form is generally for external application to the skin or mucous membranes), cream augmented (a cream dosage form that enhances drug delivery, whereby augmentation does not refer to the strength of the drug in the dosage form), emulsion (a dosage form consisting of a two-phase system comprised of at least two immiscible liquids, one of which is dispersed as droplets, internal or dispersed phase, within the other liquid, external or continuous phase, generally stabilized with one or more emulsifying agents, whereby emulsion is used as a dosage form term unless a more specific term is applicable, e.g. cream, lotion, ointment), suspensions (a liquid dosage form that contains solid particles dispersed in a liquid vehicle), suspension extended release (a liquid preparation consisting of solid particles dispersed throughout a liquid phase in which the particles are not soluble; the suspension has been formulated in a manner to allow at least a reduction in dosing frequency as compared to that drug presented as a conventional dosage form, e.g., as a solution or a prompt drug-releasing, conventional solid dosage form), pastes (A semisolid dosage form, containing a large proportion, 20-50%, of solids finely dispersed in a fatty vehicle, whereby this dosage form is generally for external application to the skin or mucous membranes), solutions (a clear, homogeneous liquid dosage form that contains one or more chemical substances dissolved in a solvent or mixture of mutually miscible solvents), powders, shampoos (a lotion dosage form which has a soap or detergent that is usually used to clean the hair and scalp; it is often used as a vehicle for dermatologic agents), shampoo suspensions (a liquid soap or detergent containing one or more solid, insoluble substances dispersed in a liquid vehicle that is used to clean the hair and scalp and is often used as a vehicle for dermatologic agents), aerosol foams (i.e., a dosage form containing one or more active ingredients, surfactants, aqueous or nonaqueous liquids, and the propellants; if the propellant is in the internal discontinuous phase, i.e., of the oil-in-water type, a stable foam is discharged, and if the propellant is in the external continuous phase, i.e., of the water-in-oil type, a spray or a quick-breaking foam is discharged), sprays (a liquid minutely divided as by a jet of air or steam), metered spray (a non-pressurized dosage form consisting of valves which allow the dispensing of a specified quantity of spray upon each activation), suspension spray (a liquid preparation containing solid particles dispersed in a liquid vehicle and in the form of coarse droplets or as finely divided solids to be applied locally, most usually to the nasal-pharyngeal tract, or topically to the skin), jellies (a class of gels, which are semisolid systems that consist of suspensions made up of either small inorganic particles or large organic molecules interpenetrated by a liquid—in which the structural coherent matrix contains a high portion of liquid, usually water), films (a thin layer or coating), film extended release (a drug delivery system in the form of a film that releases the drug over an extended period in such a way as to maintain constant drug levels in the blood or target tissue), film soluble (a thin layer or coating which is susceptible to being dissolved when in contact with a liquid), sponges (a porous, interlacing, absorbent material that contains a drug, whereby it is typically used for applying or introducing medication, or for cleansing, and whereby a sponge usually retains its shape), swabs (a small piece of relatively flat absorbent material that contains a drug, whereby a swab may also be attached to one end of a small stick, and whereby a swab is typically used for applying medication or for cleansing), patches (a drug delivery system that often contains an adhesive backing that is usually applied to an external site on the body, whereby its ingredients either passively diffuse from, or are actively transported from, some portion of the patch, whereby depending upon the patch, the ingredients are either delivered to the outer surface of the body or into the body, and whereby a patch is sometimes synonymous with the terms 'extended release film' and 'system'), patch extended release (a drug delivery system in the form of a patch that releases the drug in such a manner that a reduction in dosing frequency compared to that drug presented as a conventional dosage form, e.g., a solution or a prompt drug-releasing, conventional solid dosage form), patch extended release electronically controlled (a drug delivery system in the form of a patch which is controlled by an electric current that releases the drug in such a manner that a reduction in dosing frequency compared to that drug presented as a conventional dosage form, e.g., a solution or a prompt drug-releasing, conventional solid dosage form), and the like. The various topical dosage forms may also be formulated as immediate release, controlled release, sustained release, or the like.

The topical dosage form composition contains an active pharmaceutical ingredient and one or more inactive pharmaceutical ingredients such as excipients, colorants, pigments, additives, fillers, emollients, surfactants (e.g., anionic, cationic, amphoteric and nonionic), penetration enhancers (e.g., alcohols, fatty alcohols, fatty acids, fatty acid esters and polyols), and the like. Various FDA-approved topical inactive ingredients are found at the FDA's "The Inactive Ingredients Database" that contains inactive ingredients specifically intended as such by the manufacturer, whereby inactive ingredients can also be considered active ingredients under certain circumstances, according to the definition of an active ingredient given in 21 CFR 210.3(b)(7). Alcohol is a good example of an ingredient that may be considered either active or inactive depending on the product formulation.

As used herein, the oral dosage form includes capsules (a solid oral dosage form consisting of a shell and a filling, whereby the shell is composed of a single sealed enclosure, or two halves that fit together and which are sometimes sealed with a band, and whereby capsule shells may be made from gelatin, starch, or cellulose, or other suitable materials, may be soft or hard, and are filled with solid or liquid ingredients that can be poured or squeezed), capsule or coated pellets (solid dosage form in which the drug is enclosed within either a hard or soft soluble container or "shell" made from a suitable form of gelatin; the drug itself is in the form of granules to which varying amounts of coating have been applied), capsule coated extended release (a solid dosage form in which the drug is enclosed within either a hard or soft soluble container or "shell" made from a suitable form of gelatin; additionally, the capsule is covered in a designated coating, and which releases a drug or drugs in such a manner to allow at least a reduction in dosing frequency as compared to that drug or drugs presented as a conventional dosage form), capsule delayed release (a solid dosage form in which the drug is enclosed within either a hard or soft soluble container made from a suitable form of gelatin, and which releases a drug (or drugs) at a time other than promptly after administration, whereby enteric-coated articles are delayed release dosage forms), capsule delayed release pellets (solid dosage form in which the drug is enclosed within either a hard or soft soluble container or "shell" made from a suitable form of gelatin; the drug itself is in the form of granules to which enteric coating has been applied, thus delaying release of the drug until its passage into the intestines), capsule extended release (a solid dosage form in which the drug is enclosed within either a hard or soft soluble container made from a suitable form of gelatin, and which releases a drug or drugs in such a manner to allow a reduction in dosing frequency as compared to that drug or drugs presented as a conventional dosage form), capsule film-coated extended release (a solid dosage form in which the drug is enclosed within either a hard or soft soluble container or "shell" made from a suitable form of gelatin; additionally, the capsule is covered in a designated film coating, and which releases a drug or drugs in such a manner to allow at least a reduction in dosing frequency as compared to that drug or drugs presented as a conventional dosage form), capsule gelatin coated (a solid dosage form in which the drug is enclosed within either a hard or soft soluble container made from a suitable form of gelatin; through a banding process, the capsule is coated with additional layers of gelatin so as to form a complete seal), capsule liquid filled (a solid dosage form in which the drug is enclosed within a soluble, gelatin shell which is plasticized by the addition of a polyol, such as sorbitol or glycerin, and is therefore of a somewhat thicker consistency than that of a hard shell capsule; typically, the active ingredients are dissolved or suspended in a liquid vehicle), granule (a small particle or grain), pellet (a small sterile solid mass consisting of a highly purified drug, with or without excipients, made by the formation of granules, or by compression and molding), pellets coated extended release (a solid dosage form in which the drug itself is in the form of granules to which varying amounts of coating have been applied, and which releases a drug or drugs in such a manner to allow a reduction in dosing frequency as compared to that drug or drugs presented as a conventional dosage form), pill (a small, round solid dosage form containing a medicinal agent intended for oral administration), powder (an intimate mixture of dry, finely divided drugs and/or chemicals that may be intended for internal or external use), elixir (a clear, pleasantly flavored, sweetened hydroalcoholic liquid containing dissolved medicinal agents; it is intended for oral use), chewing gum (a sweetened and flavored insoluble plastic material of various shapes which when chewed, releases a drug substance into the oral cavity), syrup (an oral solution containing high concentrations of sucrose or other sugars; the term has also been used to include any other liquid dosage form prepared in a sweet and viscid vehicle, including oral suspensions), tablet (a solid dosage form containing medicinal substances with or without suitable diluents), tablet chewable (a solid dosage form containing medicinal substances with or without suitable diluents that is intended to be chewed, producing a pleasant tasting residue in the oral cavity that is easily swallowed and does not leave a bitter or unpleasant after-taste), tablet coated (a solid dosage form that contains medicinal substances with or without suitable diluents and is covered with a designated coating), tablet coated particles (a solid dosage form containing a conglomerate of medicinal particles that have each been covered with a coating), tablet delayed release (a solid dosage form which releases a drug or drugs at a time other than promptly after administration, whereby enteric-coated articles are delayed release dosage forms), tablet delayed release particles (a solid dosage form containing a conglomerate of medicinal particles that have been covered with a coating which releases a drug or drugs at a time other than promptly after administration, whereby enteric-coated articles are delayed release dosage forms), tablet dispersible (a tablet that, prior to administration, is intended to be placed in liquid, where its contents will be distributed evenly throughout that liquid, whereby term 'tablet, dispersible' is no longer used for approved drug products, and it has been replaced by the term 'tablet, for suspension'), tablet effervescent (A solid dosage form containing mixtures of acids, e.g., citric acid, tartaric acid, and sodium bicarbonate, which release carbon dioxide when dissolved in water, whereby it is intended to be dissolved or dispersed in water before administration), tablet extended release (a solid dosage form containing a drug which allows at least a reduction in dosing frequency as compared to that drug presented in conventional dosage form), tablet film coated (a solid dosage form that contains medicinal substances with or without suitable diluents and is coated with a thin layer of a water-insoluble or water-soluble polymer), tablet film coated extended release (a solid dosage form that contains medicinal substances with or without suitable diluents and is coated with a thin layer of a water-insoluble or water-soluble polymer; the tablet is formulated in such manner as to make the contained medicament available over an extended period of time following ingestion), tablet for solution (a tablet that forms a solution when placed in a liquid), tablet for suspension (a tablet that forms a suspension when placed in a liquid, which is formerly referred to as a 'dispersible tablet'), tablet multilayer (a solid dosage form containing medicinal substances that have been compressed to form a multiple-layered tablet or a tablet-within-a-tablet, the inner tablet being the core and the outer portion being the shell), tablet multilayer extended release (a solid dosage form containing medicinal substances that have been compressed to form a multiple-layered tablet or a tablet-within-a-tablet, the inner tablet being the core and the outer portion being the shell, which, additionally, is covered in a designated coating; the tablet is formulated in such manner as to allow at least a reduction in dosing frequency as compared to that drug presented as a conventional dosage form), tablet orally disintegrating (a solid dosage form containing medicinal substances which disintegrates rapidly, usually within a matter of seconds, when placed upon the tongue), tablet orally disintegrating delayed release (a solid dosage form containing medicinal substances which disintegrates rapidly, usually within a matter of seconds, when placed upon the tongue, but which releases a drug or drugs at a time other than promptly after administration), tablet soluble (a solid dosage form that contains medicinal substances with or without suitable diluents and possesses the ability to dissolve in fluids), tablet sugar coated (a solid dosage form that contains medicinal substances with or without suitable diluents and is coated with a colored or an uncolored water-soluble sugar), osmotic, and the like.

The oral dosage form composition contains an active pharmaceutical ingredient and one or more inactive pharmaceutical ingredients such as diluents, solubilizers, alcohols, binders, controlled release polymers, enteric polymers, disintegrants, excipients, colorants, flavorants, sweeteners, antioxidants, preservatives, pigments, additives, fillers, suspension agents, surfactants (e.g., anionic, cationic, amphoteric and nonionic), and the like. Various FDA-approved topical inactive ingredients are found at the FDA's "The Inactive Ingredients Database" that contains inactive ingredients specifically intended as such by the manufacturer, whereby inactive ingredients can also be considered active ingredients under certain circumstances, according to the definition of an active ingredient given in 21 CFR 210.3(b)(7). Alcohol is a good example of an ingredient that may be considered either active or inactive depending on the product formulation.

Treatment regimens may also include numerous dosing regimens. A description of acne vulgaris is found in *Remingtons* p. 1131. For a human, various therapeutically effective doses and dosing regimens thereof may be determined from the animal data set forth herein using known Allometric Scaling (AS) factors. For example, for a mouse having a body weight of 0.03 kg, the AS factor is around 7 assuming a human body weight of 70 kg.

The predictive dosing ranges set forth in Tables 1, 2 and 3 was calculated assuming that for the high end of the oral dose range, the top dose given to the Rhino mouse is corrected for the expected lesser sensitivity of the human and further increased by 0.5 log dose. The low dose is $1 \times 10^6$ lower than the high dose. For the high end of the topical dose, the value was further multiplied by a factor of 20 as humans absorb only about 5% of the dose compared to 100% by the mouse.

Differences in the animal species sensitivity to various vitamin D analogs as well as differences in relative absorption of various vitamin D analogs by the skin may also significantly affect the human efficacious dose compared to that used in the animal studies detailed herein.

EXAMPLES

TABLE 1

COMEDOLYTIC EFFECT OF DAILY TOPICAL APPLICATION OF
1,25-DIHYDROXYVITAMIN D3 AND ANALOGS
TO THE RHINO MOUSE

| Compound* | Comedone Area (% Vehicle)** | Dose (nmol/kg) | N |
|---|---|---|---|
| 1, 25(OH)$_2$D$_3$ | 187 ± 30 | 6.0 | 6 |
| VD-03 | 90 ± 14 | 0.62 | 6 |
| NEL | 156 ± 34 | 7.5 | 6 |
| NEL | 145 ± 24 | 25 | 6 |
| Vit-III 17-20E | 116 ± 15 | 24 | 6 |
| (24R)2MD$_2$ | 176 ± 55 | 2.3 | 6 |
| 2MPregna | 63 ± 14 | 217 | 6 |
| 2MP | 92 ± 20 | 217 | 6 |
| 2MBisP | 97 ± 9 | 22 | 6 |
| 2MBisP | 127 ± 12 | 69 | 24 |
| 2MBisP | 49 ± 3 | 217 | 36 |
| 2MBisP | 35 ± 4 | 694 | 18 |
| 2MBisP | 32 ± 7 | 2187 | 6 |
| 20R-2MBisP | 136 ± 17 | 217 | 12 |
| 20R-2MBisP | 45 ± 6 | 694 | 12 |
| 20R-2MBisP | 17 ± 3 | 2187 | 6 |
| 2MTrisP | 66 ± 9 | 217 | 6 |
| FF-44 | 104 ± 20 | 69 | 6 |
| FF-44 | 47 ± 12 | 217 | 12 |
| FF-55 | 108 ± 35 | 69 | 6 |
| FF-55 | 53 ± 8 | 217 | 12 |
| HPBS | 74 ± 10 | 217 to 122*** | 6 |

*All compounds were applied topically on a daily basis for ca. 3 weeks in vehicle comprised of 70 vol % ethanol and 30 vol % propylene glycol.
**Values are mean ± standard error of the mean
***Dose changed as indicated on day 3 (2 animals) or day 10 (4 animals) of the experiment.

TABLE 2

PREDICTIVE HUMAN ORAL DOSING RANGE

| COMPOUND | ORAL DOSING RANGE |
| --- | --- |
| 2MBisP | 7.0 mg to 7.0 ng/kg$_{BW}$/day |
| CAGE-3 | 700 ng to 0.7 pg/kg$_{BW}$/day |
| 24R-2MD$_2$ | 23 µg to 23 pg/kg$_{BW}$/day |
| VitIII (17-20E) | 230 µg to 230 pg/kg$_{BW}$/day |
| NEL | 230 µg to 230 pg/kg$_{BW}$/day |

TABLE 3

PREDICTIVE HUMAN TOPICAL DOSING RANGE

| COMPOUND | TOPICAL DOSING RANGE |
| --- | --- |
| 2MBisP | 340 mg to 0.34 µg/kg$_{BW}$/day |
| CAGE-3 | 14 µg to 14 pg/kg$_{BW}$/day |
| 24R-2MD$_2$ | 450 µg to 0.45 ng/kg$_{BW}$/day |
| VitIII (17-20E) | 4.5 mg to 4.5 ng/kg$_{BW}$/day |
| NEL | 4.5 mg to 4.5 ng/kg$_{BW}$/day |
| VD-03 | 11 µg to 0.11 ng/kg$_{BW}$/day |
| 2MPregna | 340 mg to 0.34 µg/kg$_{BW}$/day |
| 2MP | 340 mg to 0.34 µg/kg$_{BW}$/day |
| 20R-2MBisP | 340 mg to 0.34 µg/kg$_{BW}$/day |
| 2MTrisP | 34 mg to 34 ng/kg$_{BW}$/day |
| FF-44 | 340 mg to 0.34 µg/kg$_{BW}$/day |
| FF-55 | 340 mg to 0.34 µg/kg$_{BW}$/day |
| HPBS | 41 mg to 41 ng/kg$_{BW}$/day |

Rhino mice were used to topically and orally test the compounds and compositions of the invention. The Rhino mouse is a well-established animal model used to study the comedolytic effects of anti-acne agents including retinoids. (See Boulcier M et al., Experimental Models in Skin Pharmacology, 1990, *In Pharmacological Reviews* 42:127-15). Mirshahpanah and Maibach, 2007, *Cutaneous and Ocular Toxicology* 26:195-202). The Rhino mouse model was used to study the therapeutic potential of 2-Methylene-19-nor-20(S)-1α-hydroxy-bishomopregnacalciferol (2MBisP), 19-Nor-26,27-dimethylene-20(S)-2-methylene-1α,25-dihydroxyvitamin D$_3$ (CAGE-3), NEL, 24R-2MD$_2$, Vit-III (17-20E), 2MPregna, 2MP, 20R-2MbisP, 2MTrisP, FF-44, FF-55, HPBS, VD-03 and atRA. The data herein establishes that some, but not all, vitamin D analogs produce a substantial reduction in comedone size at the dose(s) tested.

Further, there is a synergistic effect by administering a combination of 2MBisP and atRA. The synergistic effect is evidenced by a substantial reduction in comedone size as compared to vehicle alone, 2MBisP alone or atRA alone. The synergistic effect is further evidenced by a substantial reduction in comedone size upon administering atRA at a low and previously-ineffective dose. By rendering such a low and previously-ineffective atRA dose now effective, potential side effects caused by administration of atRA can be minimized or avoided.

Animals and dose administration. Rhino mice 6-10 weeks old were dosed via the oral and/or topical route. In the majority of studies, the mice were dosed daily. In one topical study, the efficacy of daily versus intermittent (Monday/Wednesday/Friday) dosing was compared. The mice were weighed three times per week and doses were adjusted weekly based on body weight. The topical formulations were applied to the back of the animal in a maximum volume of 110 µL. The topical formulations were made by mixing the APIs with a topical carrier comprising 70 vol % propylene glycol and 30 vol % ethanol or 30 vol % propylene glycol and 70 vol % ethanol, as indicated. The topical vehicle control was the vehicle carrier solution matched to the formulation containing API and vehicle carrier.

The oral formulation was made by mixing the APIs with Wesson® soybean oil or NeoBee® oil. The oral dose was delivered to the back of the mouth of each mouse. Mice were sacrificed 4 hours after the final oral dose and 72 hours after the final topical dose. At sacrifice, the dorsal skin was collected for histological studies.

Figure 2:
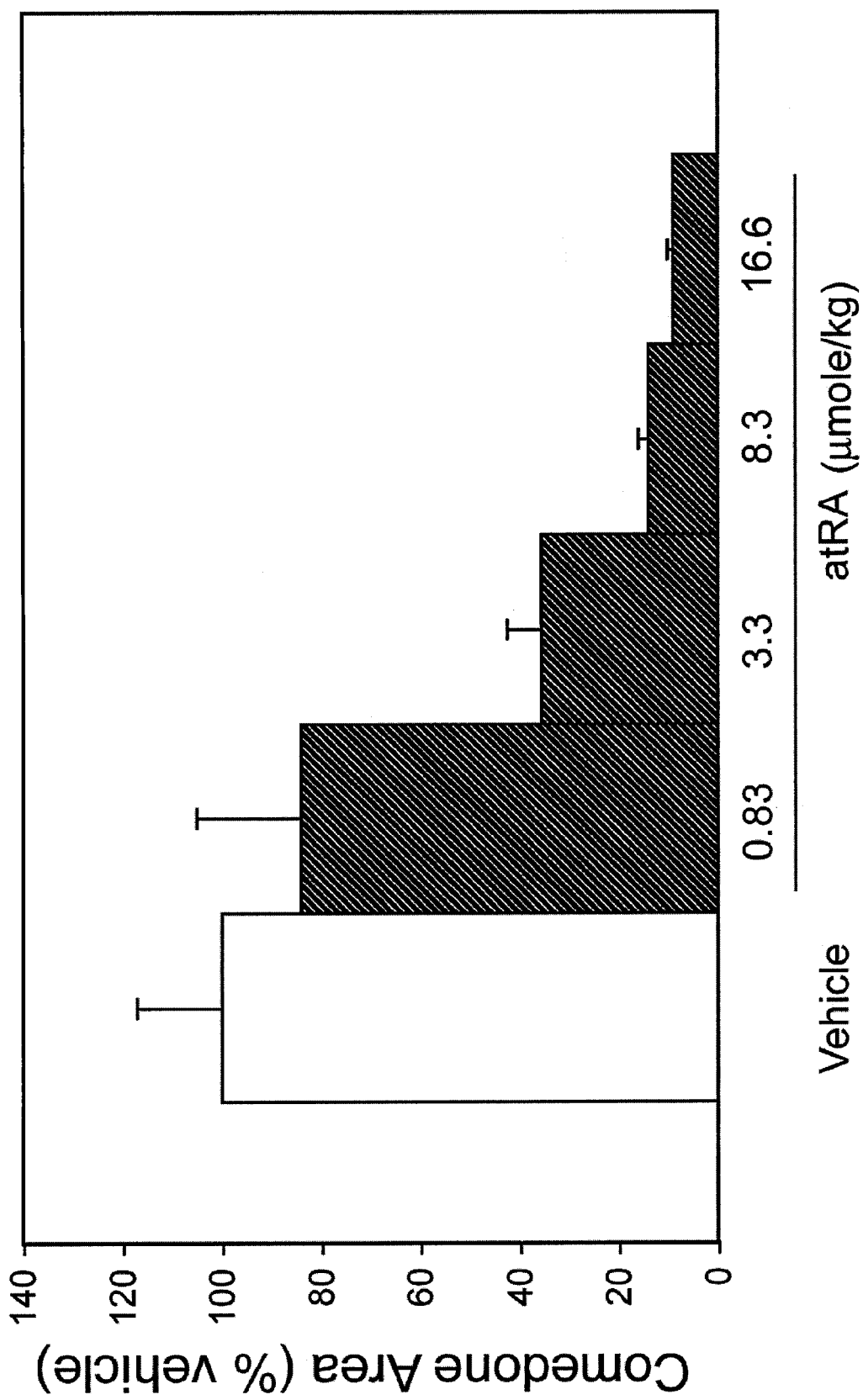
FIG. 2 is a bar graph showing treatment of Rhino mice using atRA producing a dose-dependent reduction in comedone area, whereby the comedone area was analyzed after 3 weeks of oral treatment with various doses of atRA, whereby the dose measuring 0.83 µmole/kg$_{BW}$ produced an insignificant reduction in comedone size as compared to the vehicle control, and whereby the dose measuring 16.6 µmole/kg$_{BW}$ produced a maximal reduction in comedone size as compared to the vehicle control.
Figure 3:
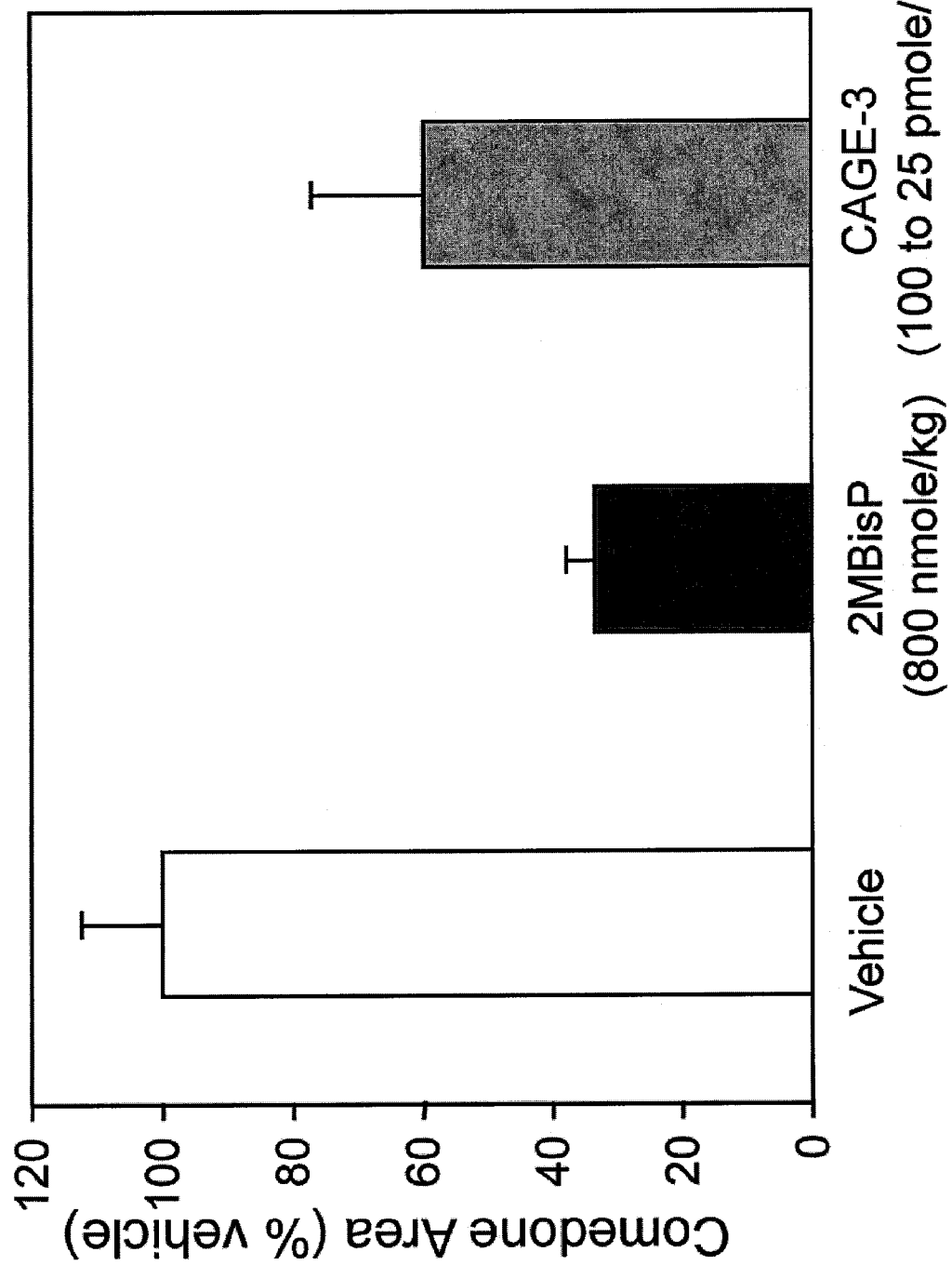
FIG. 3 is a bar graph showing topical treatment of Rhino mice using 2-methylene-19-nor-20(S)-1α-hydroxy-bishomopregnacalciferol (2MBisP) alone and 19-nor-26,27-dimethylene-20(S)-2-methylene-1α,25-dihydroxyvitamin D$_3$ (CAGE-3) alone in a carrier vehicle containing 30 vol % ethanol and 70 vol % propylene glycol producing a reduction in comedone area, whereby the comedone area was analyzed after 3 weeks of topical treatment, whereby 2MBisP was applied topically in a dose of 5.4 µg/day (ca. 800 nmole/kg$_{BW}$/day), whereby CAGE-3 was applied topically initially at dose of 0.9 ng/day (ca. 100 pmole/kg$_{BW}$/day) and at reduced doses of 0.45 ng/day beginning on day 10 and 0.22 ng/day (ca. 25 pmole/kg$_{BW}$/day) beginning on day 19 (three male mice were not treated on day 19), and whereby 2MBisP and CAGE-3 caused a reduction in the comedone area as compared to the vehicle control.
Figure 4:
FIG. 4 shows exemplary skin sections from female Rhino mice stained with haematoxylin and eosin ("H&E") after being treated with 2MBisP alone and CAGE-3 alone as described in FIG. 3, whereby treatment with 2MBisP reduced comedone area, whereby treatment with CAGE-3 also reduced comedone area, as compared to treatment with the vehicle only.
Figure 4:
Figure 4:
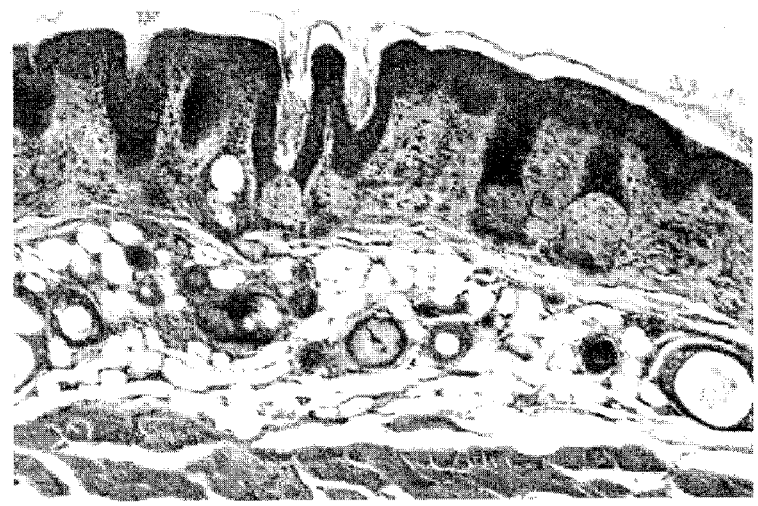
Figure 5:
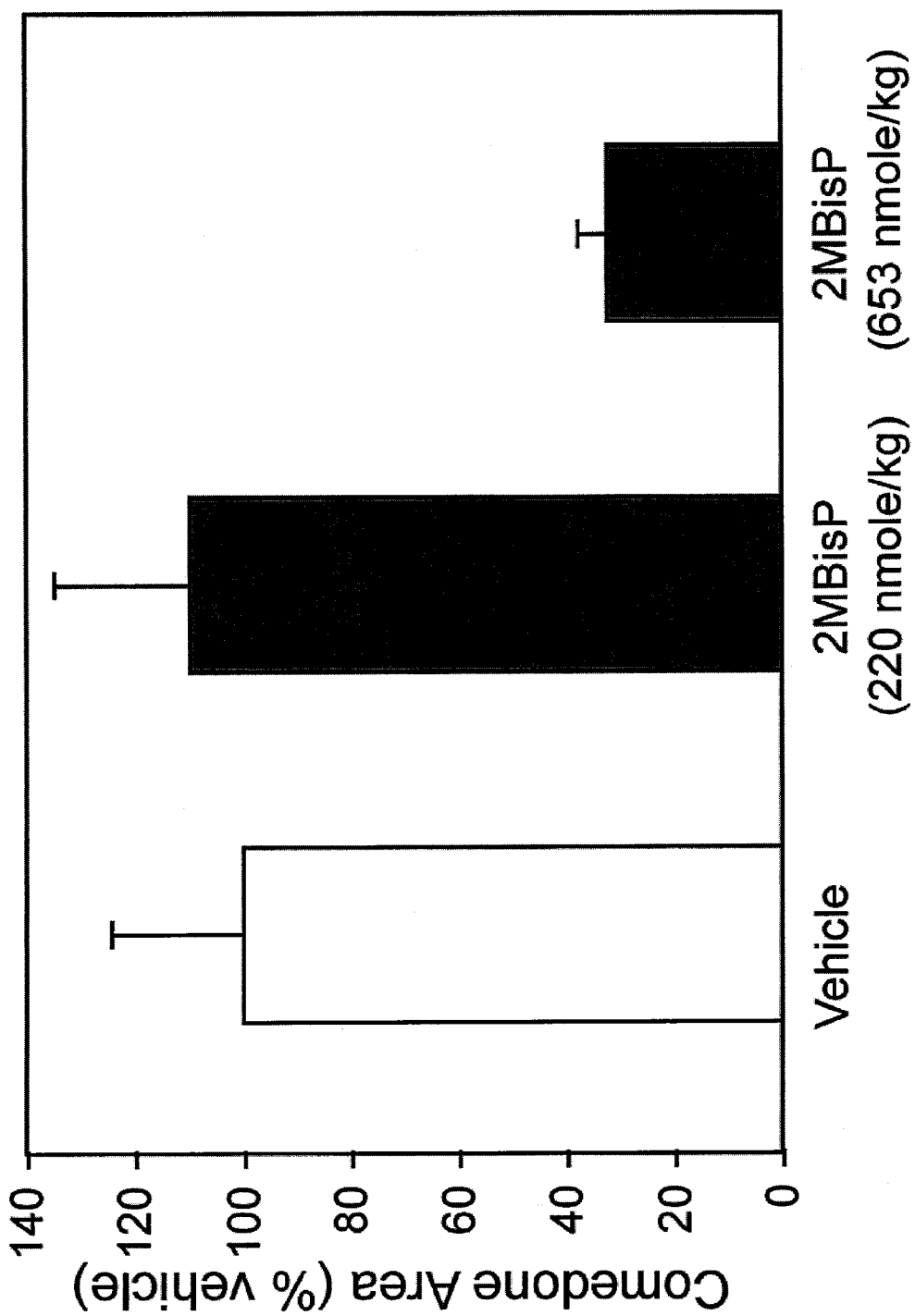
FIG. 5 is a bar graph showing comedone area for Rhino mice treated topically with 2MBisP alone at a doses of 220 mmole/kg$_{BW}$/day and 653 nmole/kg$_{BW}$/day, whereby the API was formulated in a carrier vehicle comprising 30 vol % ethanol and 70% propylene glycol, whereby comedone area was analyzed after 3 weeks of daily topical treatment, whereby the lowest dose of 2MBisP alone produced no effect, and whereby the higher dose of 2MBisP produced a near-maximal reduction in comedone area.
Figure 6:
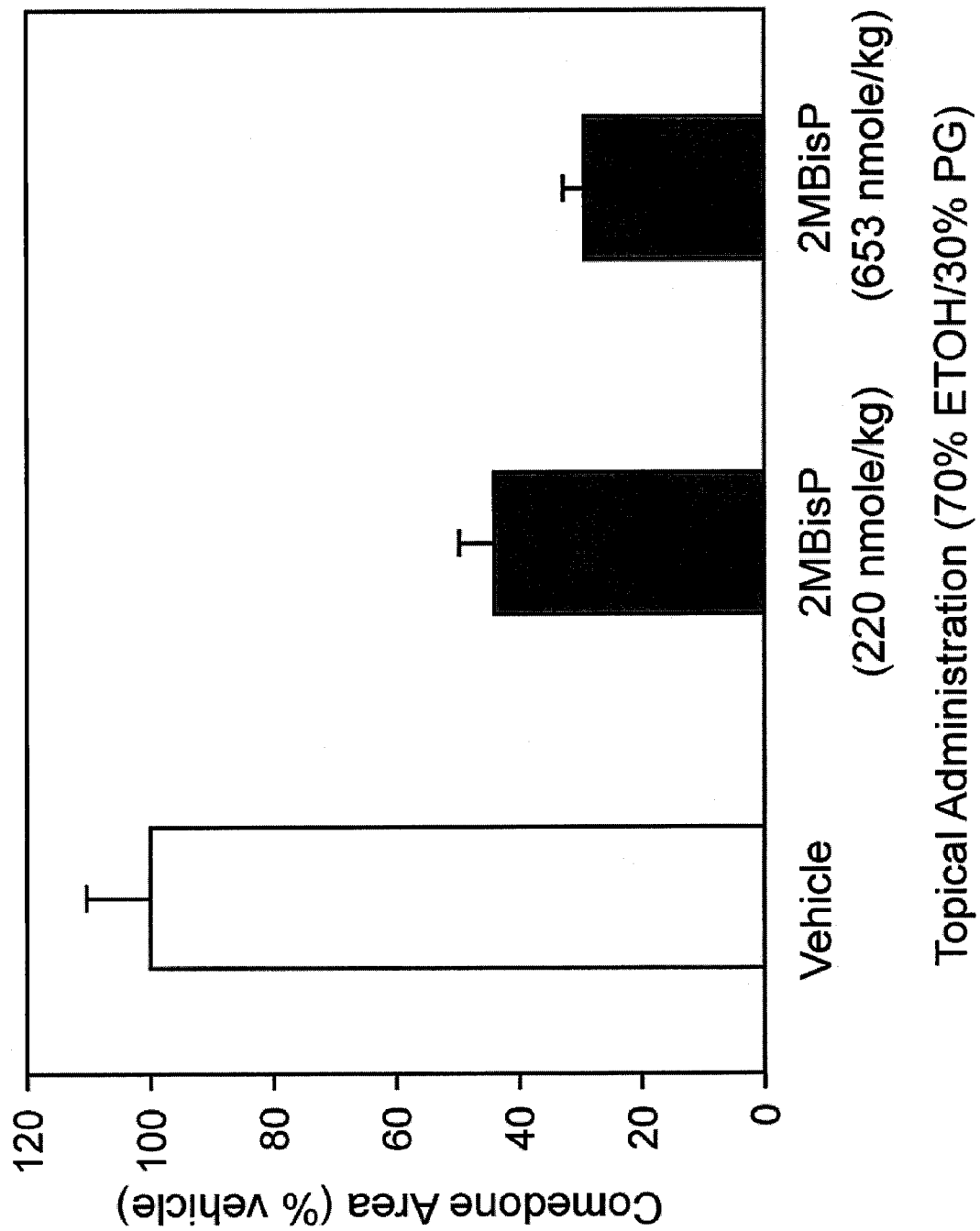
FIG. 6 is a bar graph showing comedone area for Rhino mice treated topically with 2MBisP alone at a doses of 220 nmole/kg$_{BW}$/day and 653 nmole/kg$_{BW}$/day, whereby the API was formulated in a carrier vehicle comprising 70 vol % ethanol and 30 vol % propylene glycol, whereby comedone area was analyzed after 3 weeks of daily topical treatment, whereby the topical dose of 220 nmole/kg$_{BW}$/day of 2MBisP caused over a 50% reduction in comedone area, whereby efficacy improved due to increased ethanol concentration (as compared to the carrier vehicle used in FIG. 6), and whereby the 653 nmole/kg$_{BW}$/day dose yielded greater reduction in comedone area as compared to the lower dose.
Figure 7:
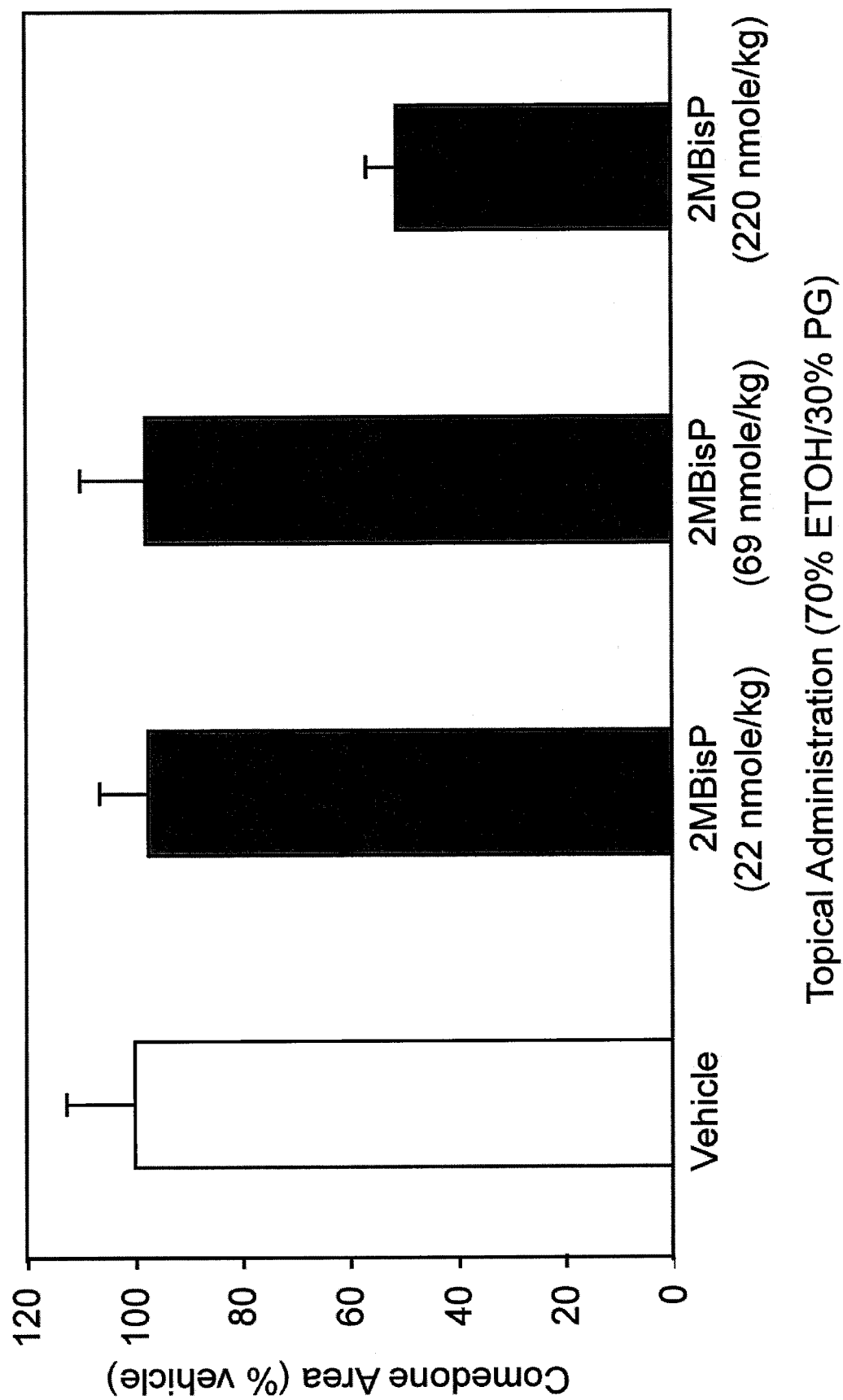
FIG. 7 is a bar graph showing comedone area for Rhino mice treated topically with 2MBisP alone at doses of 22 nmole/kg$_{BW}$/day, 69 nmole/kg$_{BW}$/day, and 220 mmole/kg$_{BW}$/day, whereby the API was formulated in a carrier vehicle comprising 70 vol % ethanol and 30 vol % propylene glycol, whereby comedone area was analyzed after 3 weeks of daily topical treatment, whereby the lower 2 doses of 2MBisP produced no effect, whereby the higher dose of 2MBisP produced a significant reduction in comedone area, and whereby efficacy improved by increasing ethanol in the carrier vehicle from 30 vol % to 70 vol %.
Figure 8:
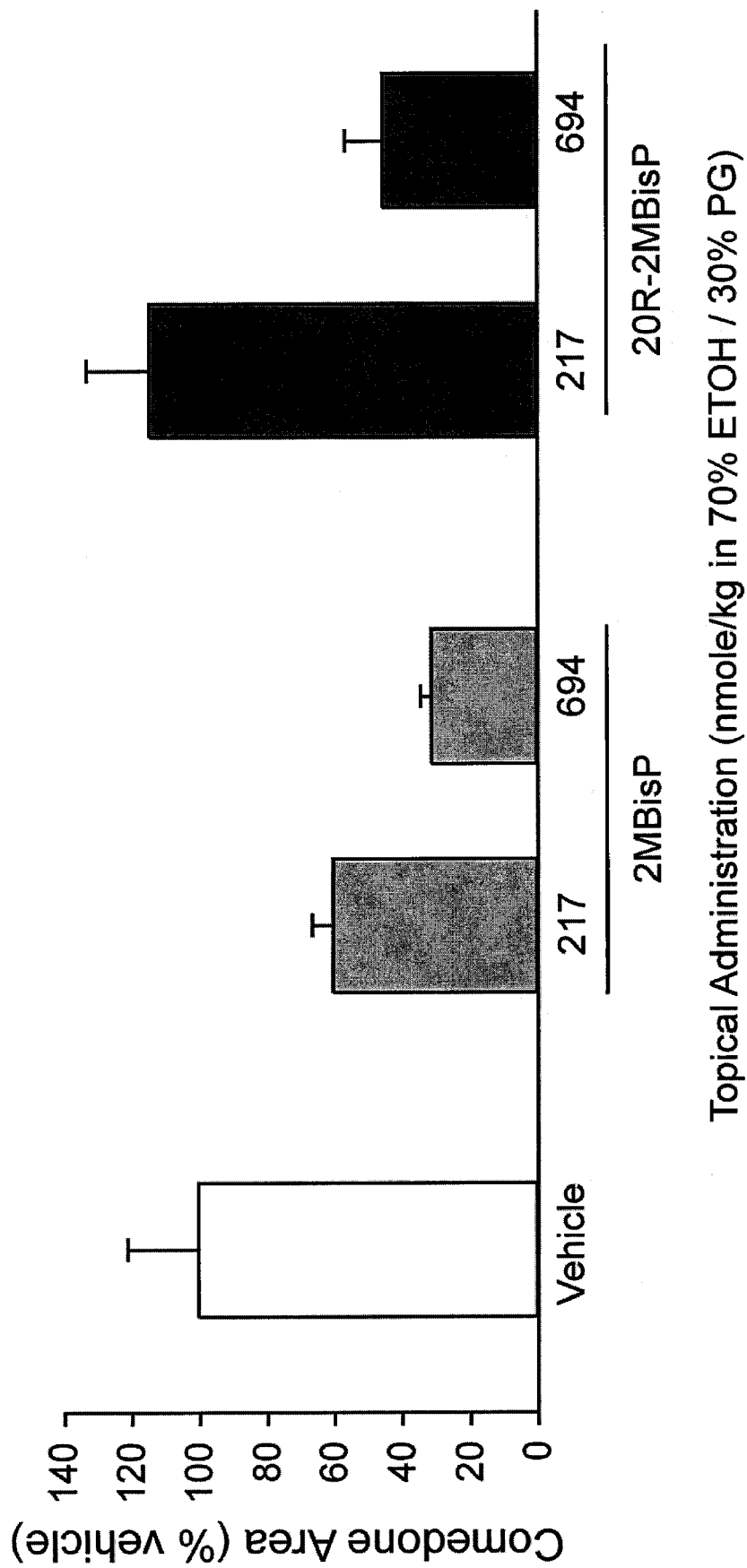
FIG. 8 is a bar graph comparing comedone area for Rhino mice treated topically with 2MBisP alone at doses of 217 nmole/kg$_{BW}$/day, and 694 mmole/kg$_{BW}$/day and other Rhino mice treated topically with 20R-2MBisP alone at doses of 217 nmole/kg$_{BW}$/day, and 694 nmole/kg$_{BW}$/day (all relative to Rhino mice treated topically with the carrier vehicle alone), whereby the API was formulated in a carrier vehicle comprising 70 vol % ethanol and 30 vol % propylene glycol, whereby comedone area was analyzed after 3 weeks of daily topical treatment, whereby both doses of 2MBisP produced a significant reduction in comedone area relative to the vehicle-treated group, whereby the lower dose of 20R-2MBisP alone produced an insignificant effect, and, whereby the higher dose of 20R-2MBisP produced a significant reduction showing that the 2MBisP with the methyl group in the 20S position is approximately ½ log more potent than the 20R-2MBisP compound in the reduction of comedone area.
Figure 9:
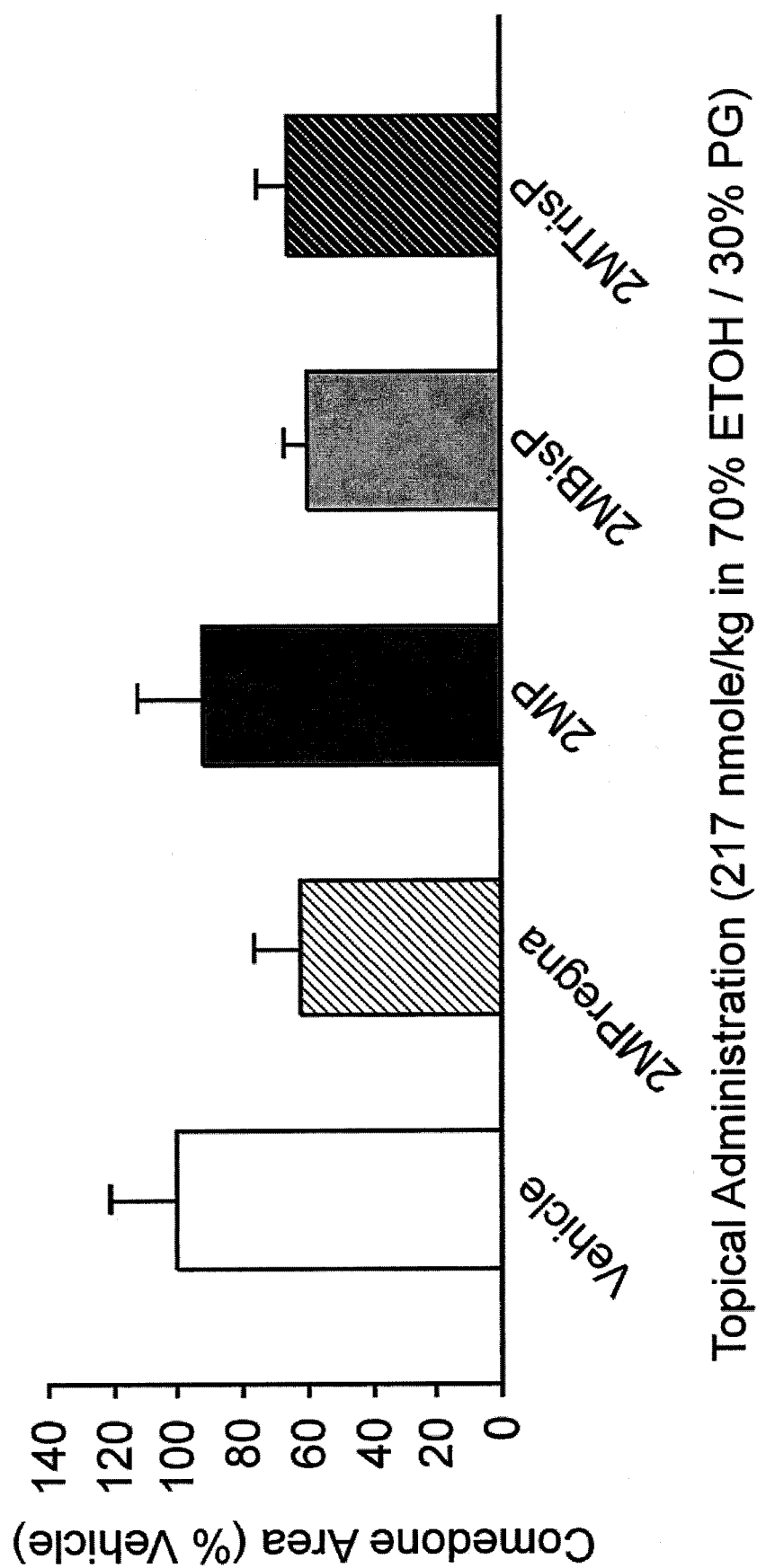
FIG. 9 is a bar graph comparing comedone area for Rhino mice treated topically with 2MPregna alone, 2MP alone, 2MBisP alone, and 2MTrisP alone at a dose of 217 nmole/kg$_{BW}$/day (all relative to Rhino mice treated topically with the carrier vehicle alone), whereby the API was formulated in a carrier vehicle comprising 70 vol % ethanol and 30 vol % propylene glycol, whereby the comedone area was analyzed after 3 weeks of daily topical treatment, whereby doses of 2MPregna, 2MBisP and 2MTrisP each produced a significant reduction in comedone area compared to those receiving vehicle alone, and whereby doses of 2MP showed a smaller reduction in comedone area.
Figure 10:
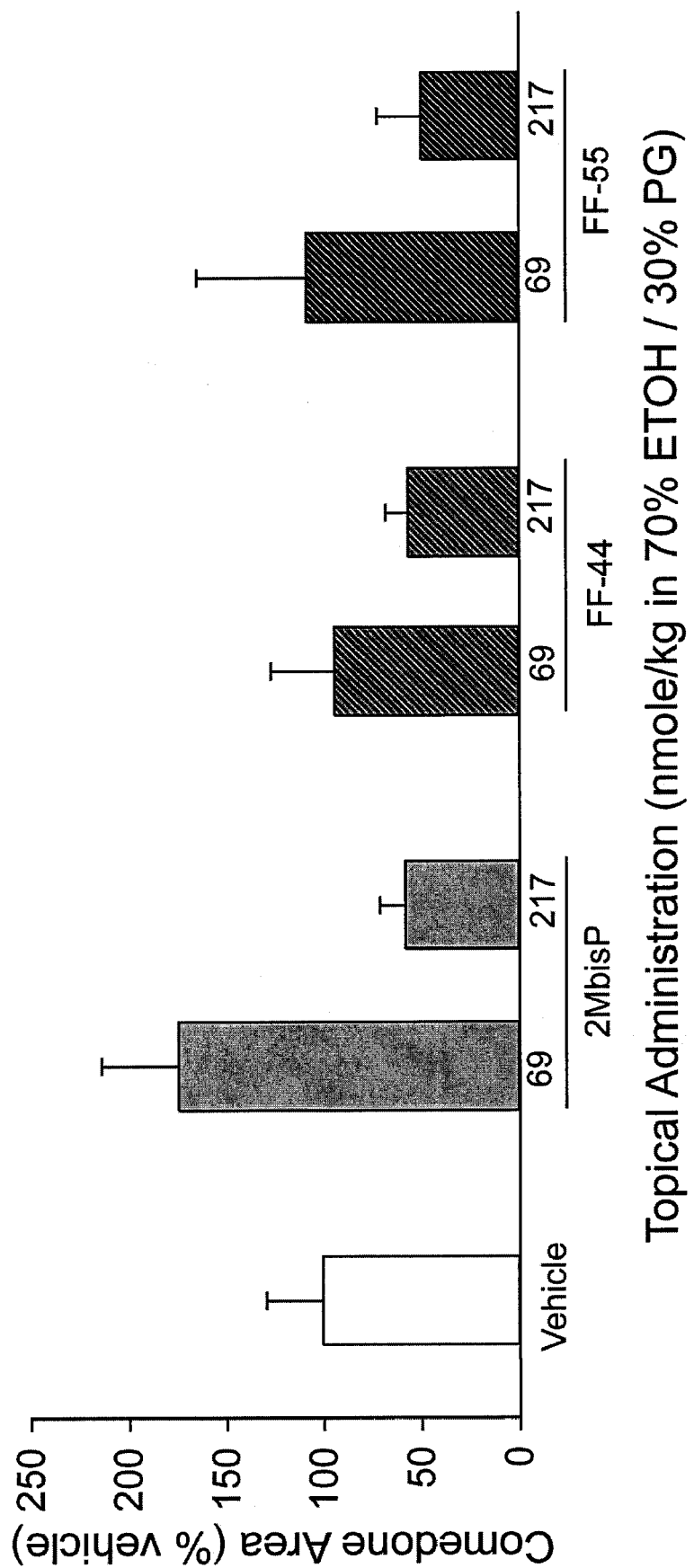
FIG. 10 is a bar graph comparing comedone area for Rhino mice treated topically with 2MBisP alone at doses of 69 mmole/kg$_{BW}$/day and 217 nmole/kg$_{BW}$/day, Rhino mice treated topically with FF-44 alone at doses of 69 nmole/kg$_{BW}$/day and 217 nmole/kg$_{BW}$/day, and Rhino mice treated topically with FF-55 alone at doses of 69 nmole/kg$_{BW}$/day and 217 nmole/kg$_{BW}$/day (all relative to Rhino mice treated topically with the carrier vehicle alone), whereby the respective API's were formulated in a carrier vehicle comprising 70 vol % ethanol and 30 vol % propylene glycol, whereby comedone area was analyzed after 3 weeks of daily topical treatment, whereby the higher doses of 2MBisP, FF-44, and FF-55 produced a significant reduction in comedone area relative to the vehicle-treated group, whereby the lower dose of 2MBisP increased comedone size, and whereby the lower doses of FF-44 alone and FF-55 produced and insignificant effect.
Figure 11:
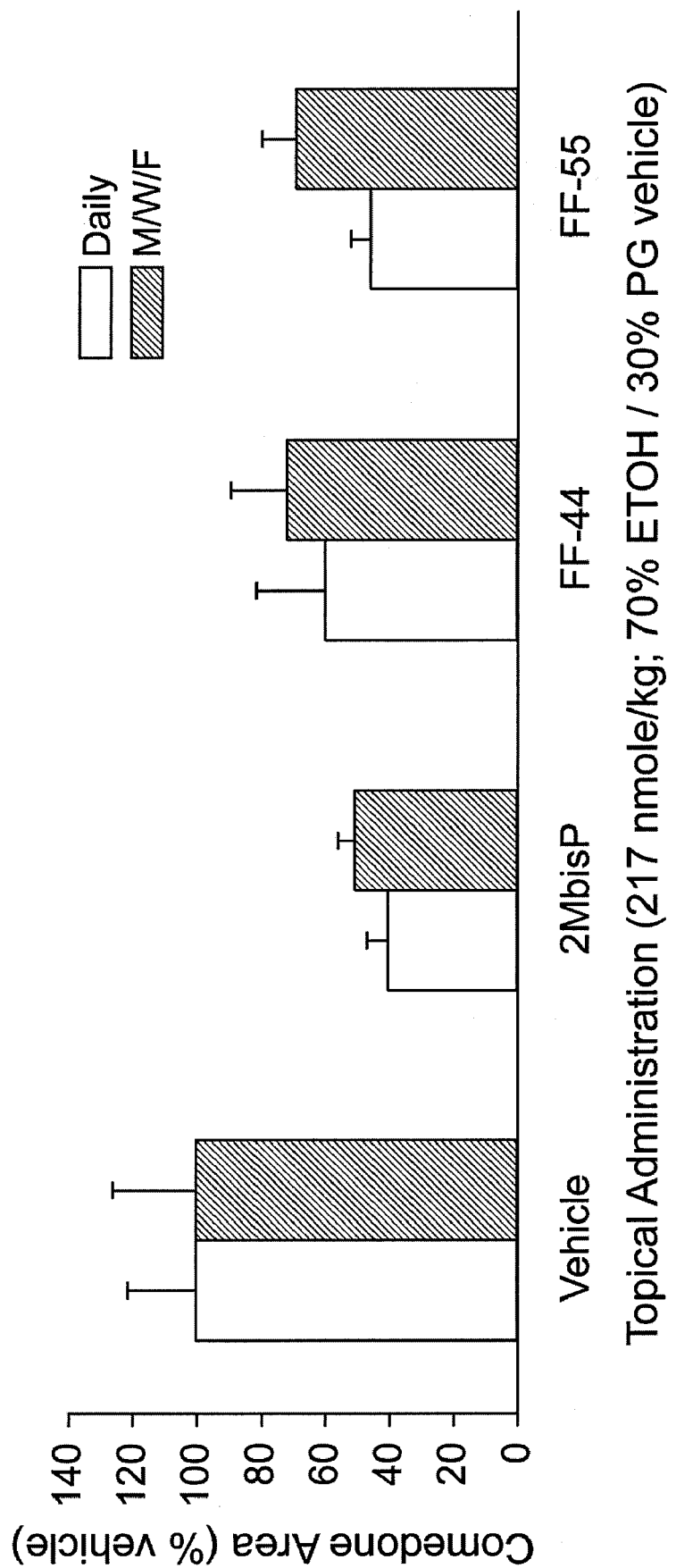
FIG. 11 is a bar graph showing comedone area for Rhino mice treated topically with 2MBisP alone, FF-44 alone, and FF-55 alone at a dose of 217 nmole/kg$_{BW}$ whereby the drug was applied either on a daily basis (total of 22 doses) or intermittently every Monday, Wednesday, and Friday (total of 10 doses), whereby the results are expressed as a percent of the vehicle-treated groups, respectively, whereby the API was formulated in a carrier vehicle comprising 70 vol % ethanol and 30 vol % propylene glycol, whereby comedone area was analyzed in skin sections taken from Rhino mice 72 h following the final topical treatment dose, whereby 2MBisP, FF-44, and FF-55 each produced a significant reduction in comedone area relative to the vehicle-treated group when applied on a daily basis, and whereby 2MBisP, FF-44, and FF-55 each produced a significant reduction in comedone area relative to the vehicle-treated group when applied intermittently as compared to daily treatment.
Figure 12:
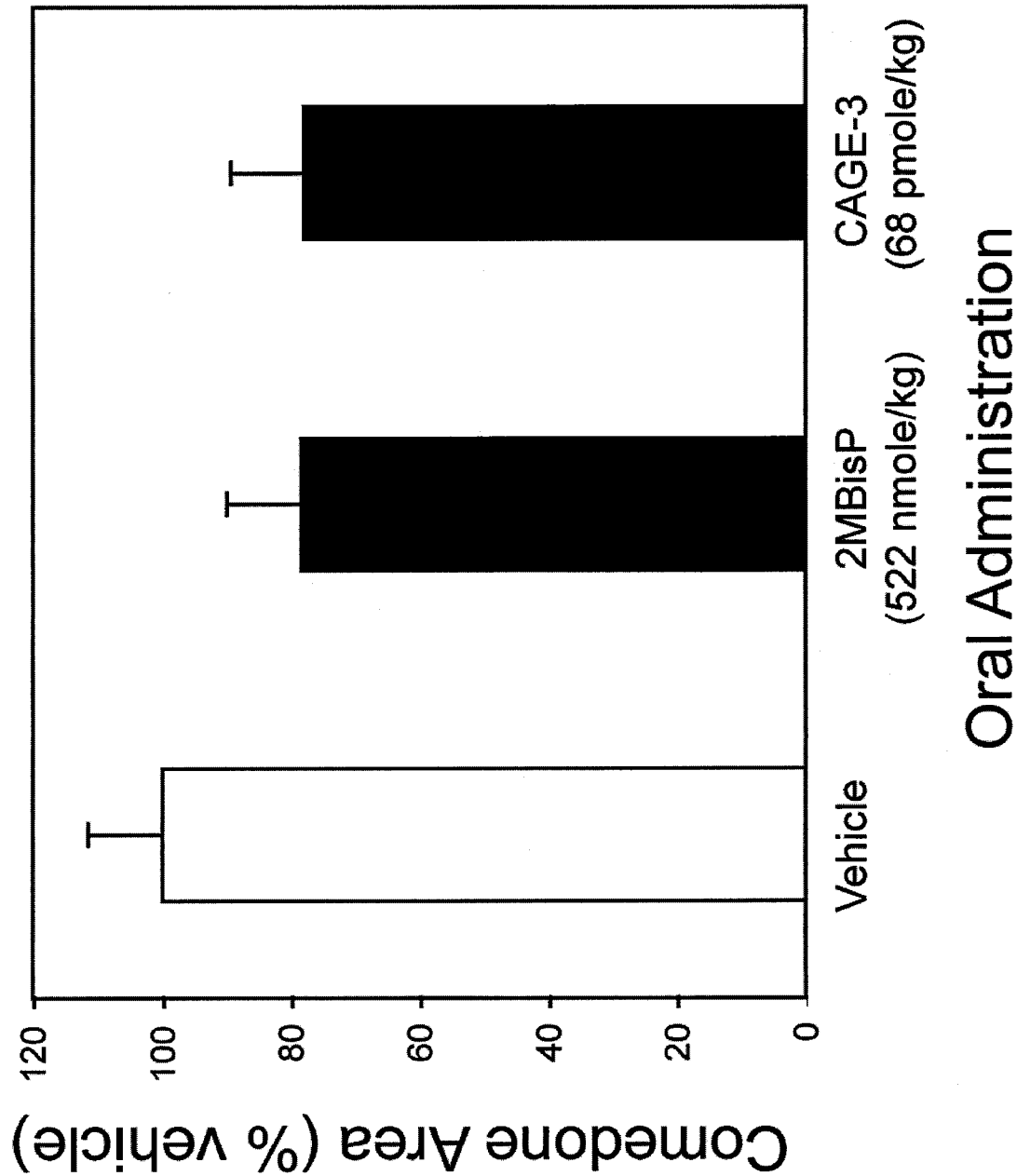
FIG. 12 is a bar graph showing the comedone area for Rhino mice treated orally with 2MBisP alone at a dose of 522 nmole/kg$_{BW}$/day and CAGE-3 alone at a dose of 68 pmole/kg$_{BW}$/day, whereby the comedone area was analyzed after 24 days of daily oral administration, and whereby both API's produced a reduction in the comedone area.
Figure 13:
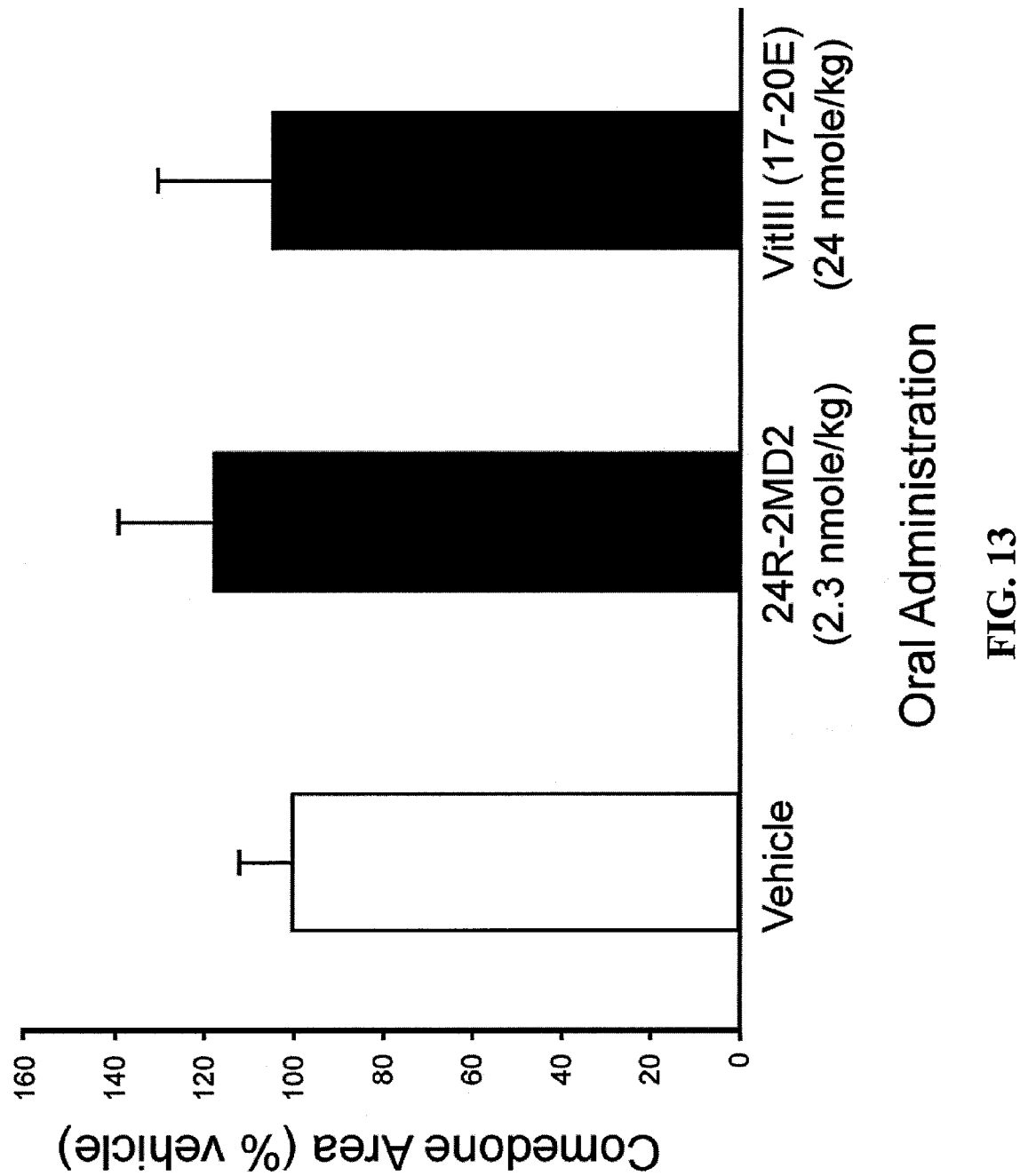
FIG. 13 is a bar graph showing comedone area for Rhino mice treated orally with 24R-2MD$_2$ alone at a dose of 2.3 nmole/kg$_{BW}$/day and VitIII (17-20E) alone at a dose of 24 nmole/kg$_{BW}$/day, whereby the comedone area was analyzed after 24 days of daily oral administration, and whereby no significant reduction in comedone area was observed.
Figure 14:
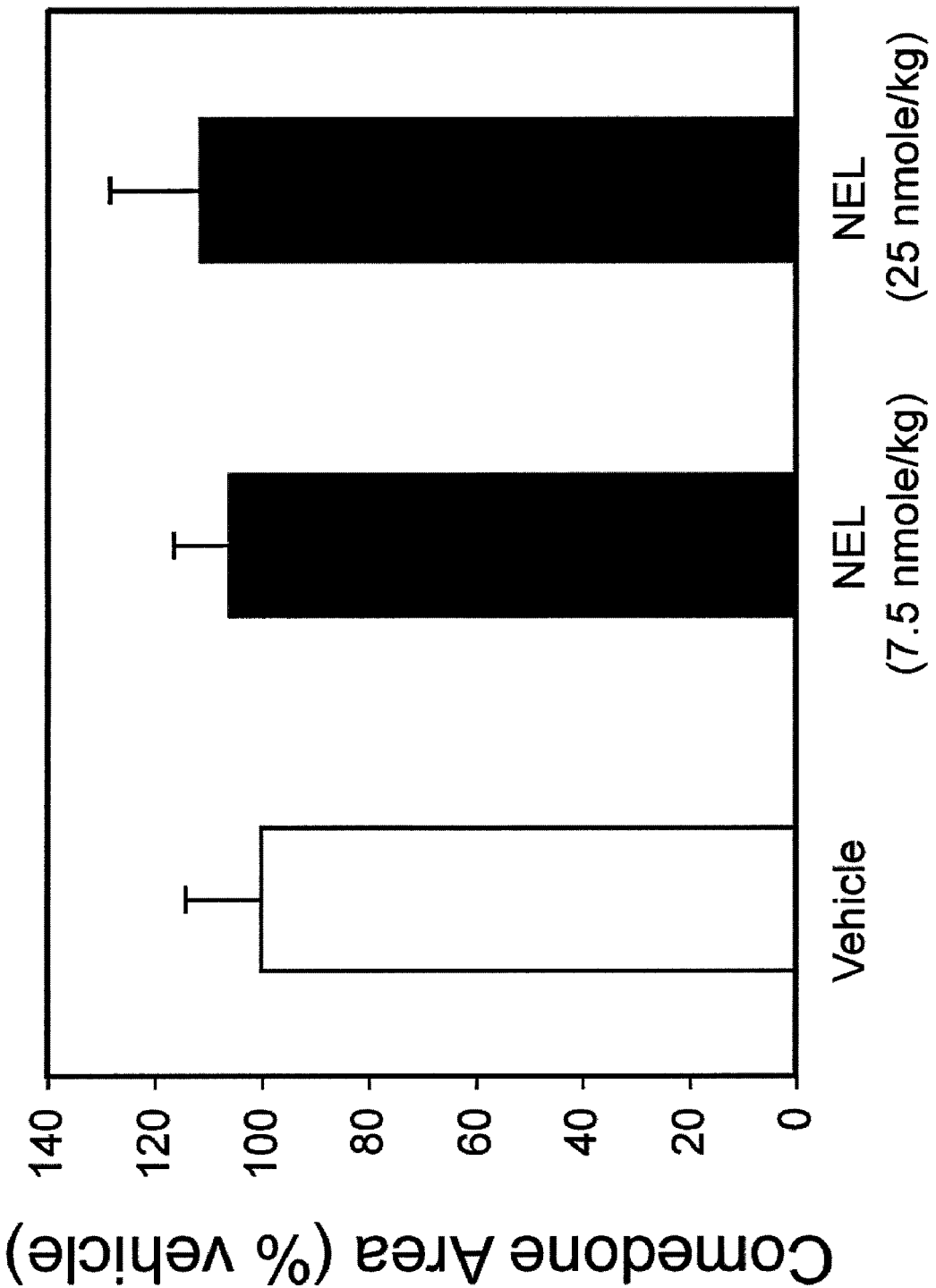
FIG. 14 is a bar graph showing comedone area for Rhino mice treated orally with NEL alone at doses of 7.5 nmole/kg$_{BW}$/day and 25 nmole/kg$_{BW}$/day, whereby the comedone area was analyzed after 24 days of daily oral administration, and whereby no significant reduction in comedone area was observed.
Figure 15:
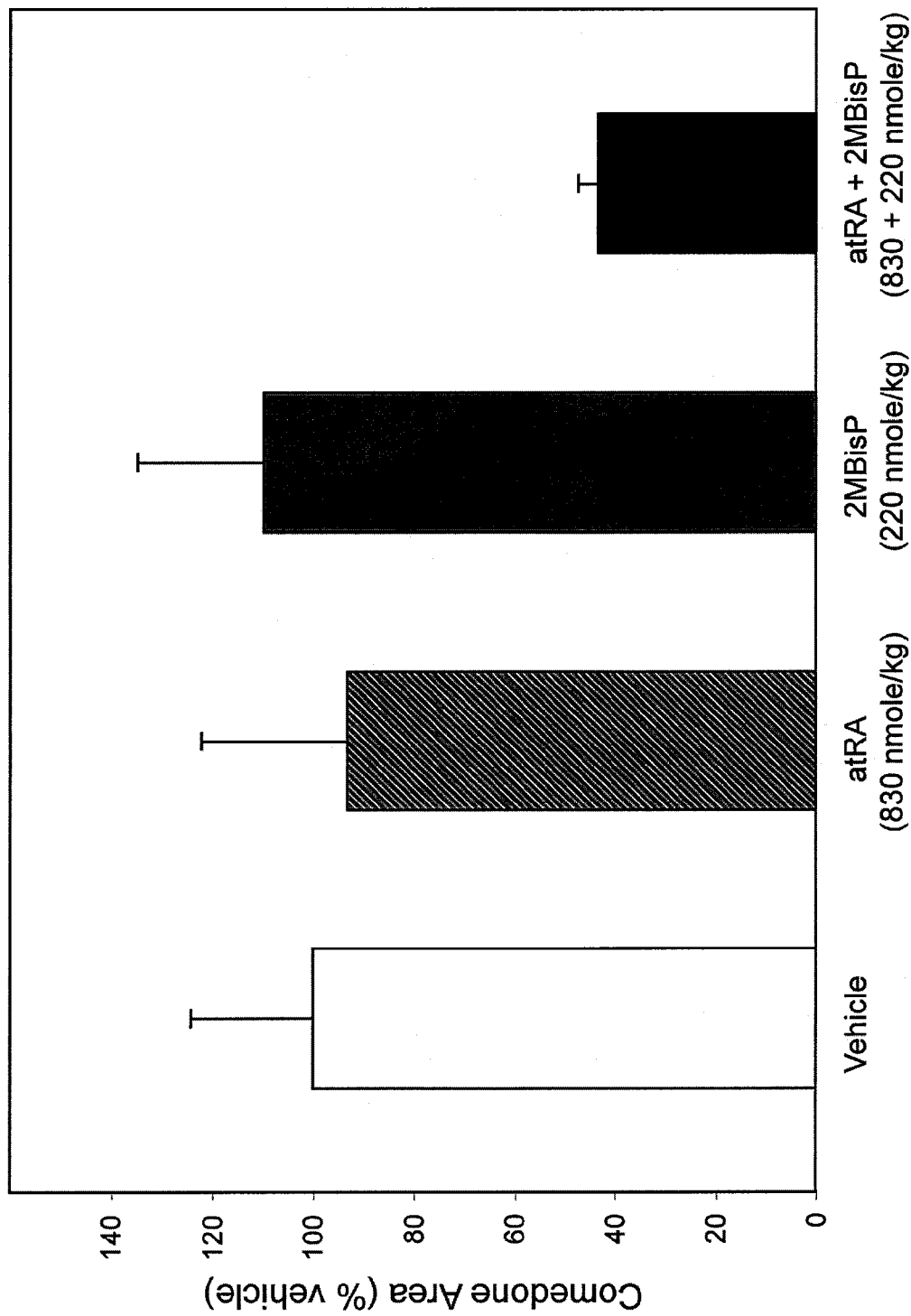
FIG. 15 is a bar graph showing the comedone area of Rhino mice orally treated with atRA alone for 24 days and receiving the topical vehicle for 21 days, Rhino mice topically treated with 2MBisP alone for 21 days in carrier (30 vol % ethanol and 70 vol % propylene glycol) and receiving the oral vehicle for 24 days, and Rhino mice orally treated with atRA for 24 days in combination with being topically treated with 2MBisP for 21 days, whereby comedone area was analyzed in skins taken from Rhino mice 4 hours after the final oral dose of vehicle or atRA, whereby the combination therapy using atRA and 2MBisP synergistically reduced comedone area, whereby treatment using the oral dose of atRA alone with the topical vehicle lacked significant efficacy, whereby the topical dose of 2MBisP alone with the oral vehicle lacked significant efficacy, and whereby treatment using atRA alone or 2MBisP alone lacked significant efficacy in view of the vehicle control group.
Figure 16:
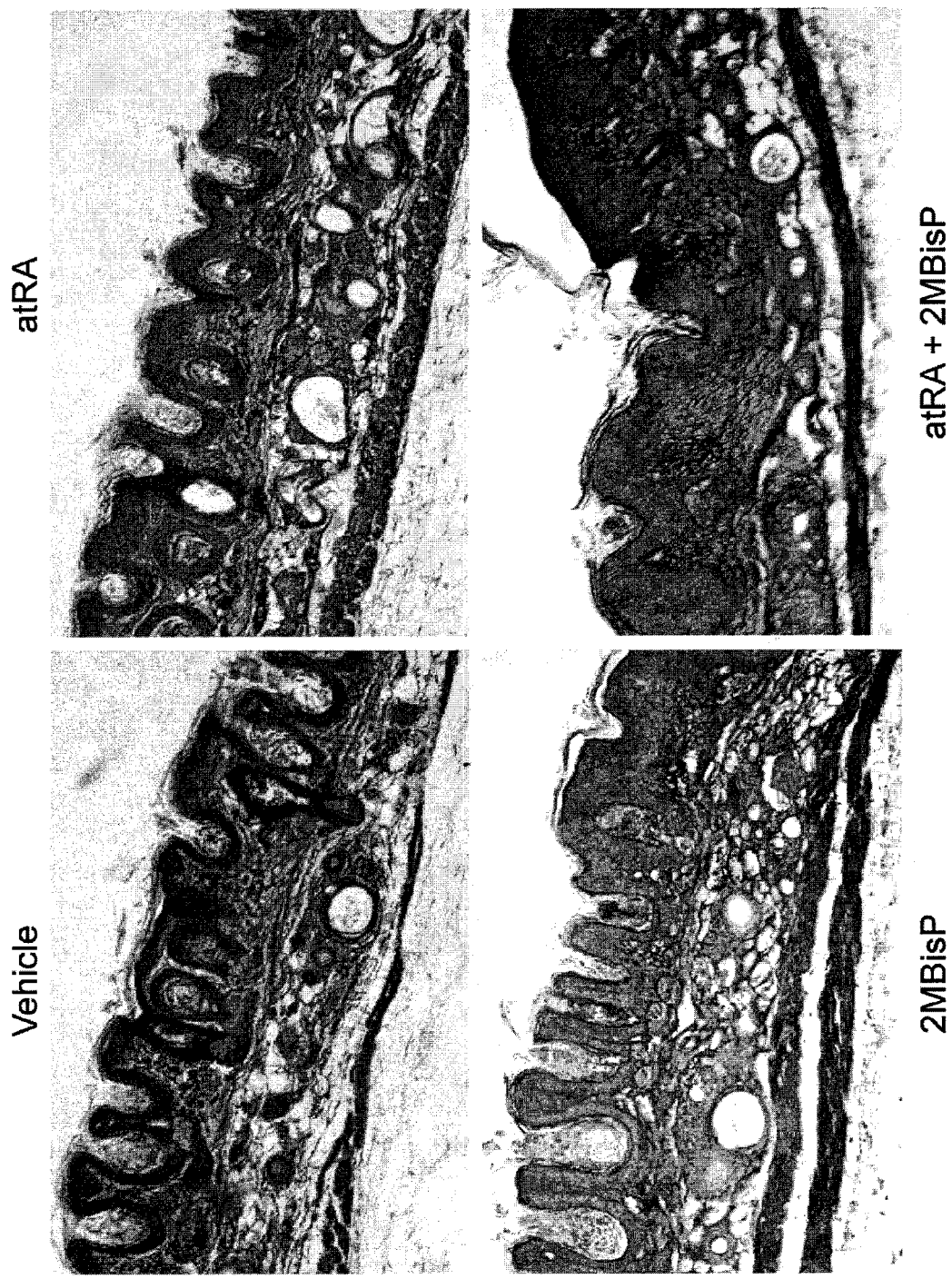
FIG. 16 illustrates skin sections from female Rhino mice stained with H&E, whereby the mice were treated orally with atRA alone (830 nmole/$kg_{BW}$/day) in an oral vehicle (Wesson® soybean oil), topically with 2MBisP alone (0.22 µmole/$kg_{BW}$/day) in a topical vehicle (30% ethanol and 70% propylene glycol), and a combination of atRA orally and 2MBisP topically, whereby atRA treatment alone did not alter skin morphology significantly as compared to the vehicle control, whereby the 2MBisP topical treatment alone did not alter skin morphology significantly, and whereby treatment with the combination of atRA and 2MBisP unexpectedly, synergistically and significantly reduced the comedone area and the number of comedones.

Comedolytic effect. The extent of the comedolytic effect (i.e., efficacy) was assessed by measuring the average area of the comedones, whereby the smaller the area, the larger the effect. The comedone area was determined by histological analysis of tissue sections based on a method developed in our lab (see FIG. 2). Skin was fixed overnight in 4% paraformaldehyde at 4 deg. C. with gentle agitation and dehydrated the next day into 100% methanol. Samples were embedded in paraffin and a total of nine 10 micron sections 150 microns apart were prepared from each Rhino mouse. Five of the nine sections were digitally imaged (6× magnification) for comedone analysis using Metamorph Imaging Software (trace function). The perimeter of each comedone on the images taken from the 5 sections was then traced using a Wacom Intuos 3 Graphics Tablet interfaced with the software. The number of pixels comprising the area of each individual comedone was obtained and transferred to an Excel spreadsheet, and the mean number of pixels per comedone was obtained for each Rhino mouse. For comedones that were completely healed (area=0) a pixel value approaching 0 (<10) was entered into the spreadsheet. The individual comedone area average for each mouse was then used to calculate the treatment group mean. Results in the figures are expressed in terms of mean ±standard error of the mean.

Preparation of oral dosing solutions containing 2MBisP, CAGE-3, 24R-2MD$_2$, VitIII (17-20E) and NEL. Separate concentrated stocks of 2MBisP, CAGE-3, 24R-2MD$_2$, VitIII (17-20E) and NEL were obtained in ethanol. The concentration was determined spectrophotometrically using a molar extinction coefficient=42,000 and $\lambda_{max}$=252.7. Oral dosing solutions were prepared by adding the appropriate volume of the ethanolic solution to oil (NeoBee® or Wesson®) whereby the final concentration of ethanol does not exceed 5 vol %. The final dose was delivered in <50 µL of oil.

Preparation of topical formulations containing 2MBisP, CAGE-3, 24R-2MD$_2$, VitIII (17-20E), NEL, VD-03, 2MPregna, 2MP, 20R-2MBisP, 2MTrisP, FF-44, FF-55, and HPBS. Separate concentrated ethanolic stocks of 2MBisP, CAGE-3, 24R-2MD$_2$, VitIII (17-20E) and NEL were diluted to a final concentration containing 70 vol % propylene glycol and 30 vol % ethanol or 30 vol % propylene glycol and 70 vol % ethanol as the excipient carrier system. The mixture was thoroughly mixed. The topical dosing formulation delivered the desired dosing amount of drug on a per kilogram body weight basis. A dose ranging from 100-110 µL in volume was administered to the back of the mouse. An average weight of 24 or 30 g/mouse was assumed in dose volume calculations. Dosing volumes were adjusted weekly to deliver the desired dosing amount of API based on the body weight of each individual animal.

Preparation of oral atRA dosing formulation. A concentrated stock solution containing atRA was prepared in dichloromethane. The atRA concentrated stock solution was diluted into ethanol. The concentration of atRA in that diluted stock solution was determined spectrophotometrically, whereby the molar extinction coefficient=45,200 and $\lambda_{max}$=350. The purity of atRA was determined to be >99% by HPLC. The appropriate volume of atRA was added to Wesson® oil, the sample was mixed, and the residual dichloromethane was removed by flushing the oil with argon for 3 hours under a vapor hood. The final dose was delivered orally using ≦50 μL of oil.

Methods. Animals and dose administration. Rhino mice 6-10 weeks old were dosed via the oral route. The mice were dosed daily. The mice were weighed three times per week and doses were adjusted weekly based on body weight. The oral formulation was made by mixing the APIs with Wesson® soybean oil. The oral dose was delivered to the back of the mouth of each mouse. Mice were sacrificed 4 hours after the final oral dose. At sacrifice, the dorsal skin was collected for histological studies.

We claim:

1. A topical composition for use in treating acne, the composition comprising a therapeutically effective dose of

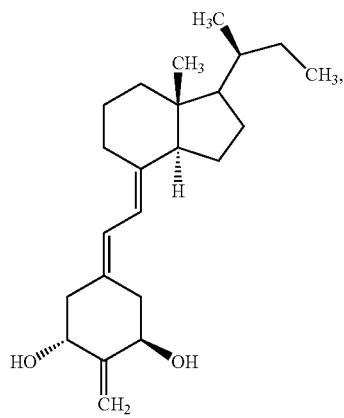

a stereoisomer thereof, or a salt thereof, wherein the effective dose is at least 116 mcg/day, and a pharmaceutically suitable topical carrier system.

2. The topical composition of claim 1, wherein the carrier system comprises 30% to 70% ethanol and 70% to 30% propylene glycol.

3. The topical composition of claim 1, wherein the carrier system comprises 70% ethanol and 30% propylene glycol.

4. A method of treating acne comprising topically administering daily or intermittently the composition of claim 1 to a human.

5. A method of reducing comedone area comprising topically administering daily or intermittently the composition of claim 1 to a human.

6. A method of treating psoriasis comprising topically administering daily or intermittently the composition of claim 1 to a human.

7. A method of treating ichthyosis comprising topically administering daily or intermittently the composition of claim 1 to a human.

8. A method of treating photoaging or photodamaged skin comprising topically administering daily or intermittently the composition of claim 1 to a human.

9. A method of treating skin cancer comprising topically administering daily or intermittently the composition of claim 1 to a human.

10. A pharmaceutical kit comprising:
a topical dosage form composition comprising a therapeutically effective dose of an active pharmaceutical ingredient comprising a compound according to the formula

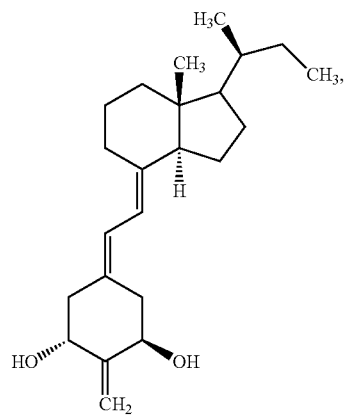

a stereoisomer thereof, a salt thereof, or a solute thereof, wherein the effective dose is at least 116 mcg/day, and, a pharmaceutically suitable topical carrier system.

11. The kit of claim 10, wherein the topical carrier system comprises 30% to 70% ethanol and 70% to 30% propylene glycol.

12. The kit of claim 11, wherein the topical carrier system comprises 70% ethanol and 30% propylene glycol.

13. A pharmaceutical kit comprising:
a topical dosage form composition comprising a therapeutically effective dose of a compound according to the formula

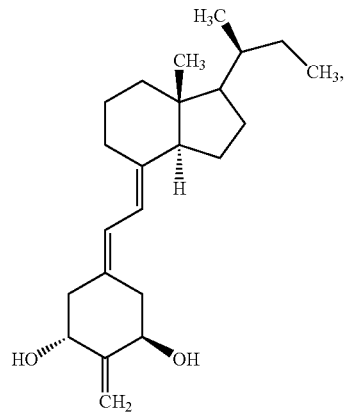

a stereoisomer thereof, a salt thereof, or a solute thereof, wherein the effective dose is at least 116 mcg/day, and, a pharmaceutically suitable topical carrier system.

14. The pharmaceutical kit of claim 13, wherein the topical carrier system comprises 30% to 70% ethanol and 70% to 30% propylene glycol.

15. The pharmaceutical kit of claim 14, wherein the topical carrier system comprises 70% ethanol and 30% propylene glycol.

16. A method of treating acne comprising administering daily or intermittently the kit of claim 10 to a human.

17. A method of reducing comedone area comprising administering daily or intermittently the kit of claim 10 to a human.

18. A method of treating psoriasis comprising administering daily or intermittently the kit of claim 10 to a human.

19. A method of treating ichthyosis comprising administering daily or intermittently the kit of claim 10 to a human.

20. A method of treating photoaging or photodamaged skin comprising administering daily or intermittently the kit of claim 10 to a human.

21. A method of treating skin cancer comprising administering daily or intermittently the kit of claim 10 to a human.

22. A topical composition for use in treating acne, the composition comprising a therapeutically effective dose of

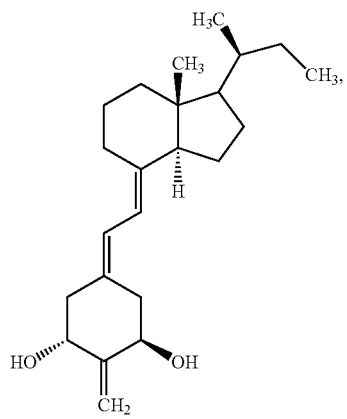

a stereoisomer thereof, or a salt thereof, wherein the therapeutically effective dose is in the range of 116 mcg/day to 3,672 mcg/day, and a pharmaceutically suitable topical carrier system.

23. A topical composition for use in treating acne, the composition comprising a therapeutically effective dose of

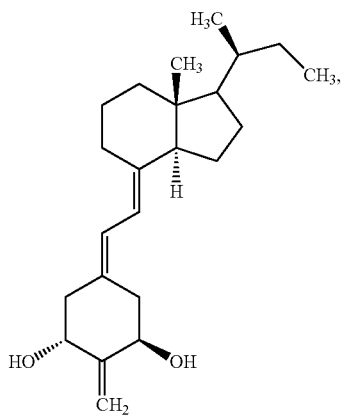 [SMILES: C=C1[C@H](O)CC(=C/C=C2\CCC[C@]3(C)C([C@@H](C)CC)CC[C@@H]23)C[C@H]1O]

a stereoisomer thereof, or a salt thereof, wherein the therapeutically effective dose is in the range of 1,428 mcg/day to 45,180 mcg/day, and a pharmaceutically suitable topical carrier system.

* * * * *

UNITED STATES PATENT AND TRADEMARK OFFICE
CERTIFICATE OF CORRECTION

Page 1 of 1

PATENT NO. : 8,404,667 B2
APPLICATION NO. : 11/966504
DATED : March 26, 2013
INVENTOR(S) : Clagett-Dame et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 317 days.

Signed and Sealed this
Eighteenth Day of November, 2014

Michelle K. Lee
*Deputy Director of the United States Patent and Trademark Office*